US008527297B2

(12) United States Patent
Whalen et al.

(10) Patent No.: US 8,527,297 B2
(45) Date of Patent: Sep. 3, 2013

(54) METHODS, APPARATUSES, AND COMPUTER PROGRAM PRODUCTS FOR FACILITATING CO-MORBID CARE MANAGEMENT

(75) Inventors: Matt Whalen, Louisville, CO (US); Carolee Strom, Boulder, CO (US); Domingo Polican, Peoria, AZ (US)

(73) Assignee: McKesson Financial Holdings, Hamilton (BM)

( * ) Notice: Subject to any disclaimer, the term of this patent is extended or adjusted under 35 U.S.C. 154(b) by 454 days.

(21) Appl. No.: 12/568,908

(22) Filed: Sep. 29, 2009

(65) Prior Publication Data

US 2011/0077955 A1 Mar. 31, 2011

(51) Int. Cl.
*G06Q 10/00* (2012.01)
*G06Q 50/00* (2012.01)
(52) U.S. Cl.
USPC .................................................. 705/2; 705/3
(58) Field of Classification Search
USPC ........................................................ 705/2, 3
See application file for complete search history.

(56) References Cited

U.S. PATENT DOCUMENTS

2007/0033072 A1\* 2/2007 Bildirici ............................ 705/3
2010/0332250 A1\* 12/2010 Simpson et al. ................... 705/2

\* cited by examiner

*Primary Examiner* — Robert Morgan
*Assistant Examiner* — Maroun Kanaan
(74) *Attorney, Agent, or Firm* — Alston & Bird LLP

(57) ABSTRACT

Methods, apparatuses, and computer program products are provided for facilitating co-morbid care management. A method may include determining a plurality of medical conditions affecting a member enrolled in a care management plan. The method may further include activating, based at least in part upon the determined medical conditions, a plurality of member assessment modules. Each activated member assessment module may be associated with a respective determined medical condition and may comprise a set of assessment questions targeted to the medical condition with which the member assessment module is associated. The method may additionally include generating a blended co-morbid assessment question set based at least in part on the assessment question sets of the activated member assessment modules by blending the assessment question sets of the activated member assessment modules into a blended co-morbid assessment question set. Corresponding apparatuses and computer program products are also provided.

17 Claims, 29 Drawing Sheets

POPULATION CARE MANAGEMENT

McKESSON
*EMPOWERING HEALTHCARE*
*POPULATION CARE MANAGEMENT*

| MAP | DEMOGRAPHICS | MEDICATION | UTILIZATION | CARE COORDINATION | ALERTS | PROVIDERS | END CONTACT | CANCEL |

JANE DOE, 39 YEARS OLD.
BELONGS TO MY TEST CLIENT.
HISTORY

CALL TIME: 00:05:37
CALL TYPE: INITIAL ASSESSMENT
RISK: 1
PRODUCT: CHRONIC CARE MANAGEMENT
DATE ENROLLED: 06/09/2009

CALL ACTIVITIES
- ☑ INTRODUCTION
- ☑ MEDICAL HISTORY
- ☑ TREATMENT INDICATION
- ① INITIAL ASSESSMENT

[UPDATE]

REMINDERS
NO REMINDERS

[NEW...]

LABS

MEMBER LABS

HgbA1c
| SOURCE | LAB DATE | HgbA1c |
|---|---|---|
| M | 0 TO 6 MONTHS | 7 PERCENT |

OPTIONAL

CURRENT WEIGHT
| SOURCE | LAB DATE | WEIGHT | BMI |
|---|---|---|---|
| M | 0 TO 6 MONTHS | 120 POUNDS | |

LIPIDS
| SOURCE | LAB DATE | LDL | TOTAL | HDL | TRIGLYCERIDES |
|---|---|---|---|---|---|
| M | >12 MONTHS | mg/dL | mg/dL | mg/dL | mg/dL |

BLOOD PRESSURE
| SOURCE | LAB DATE | SYSTOLIC | DIASTOLIC |
|---|---|---|---|
| M | 06/09/2009 | 120 mm Hg | 75 mm Hg |

LABS AND EXAMS     0 OF 6
OTHER METRICS      OPTIONAL
MEMBER ACTIVITY PLAN (MAP)

CALL NOTES
[SPELL]

[DONE]

*FIG. 10*

POPULATION CARE MANAGEMENT

McKESSON
*EMPOWERING HEALTHCARE*
*POPULATION CARE MANAGEMENT*

JANE DOE, 39 YEARS OLD.
BELONGS TO MY TEST CLIENT.
HISTORY

CALL TIME: 00:04:55
CALL TYPE: INITIAL ASSESSMENT
RISK: 3
PRODUCT: CHRONIC CARE MANAGEMENT
DATE ENROLLED: 06/09/2009

[MAP] [DEMOGRAPHICS] [MEDICATION] [UTILIZATION] [CARE COORDINATION] [ALERTS] [PROVIDERS] [END CONTACT] [CANCEL]

CALL ACTIVITIES
- ☑ INTRODUCTION
- ☑ MEDICAL HISTORY
- ☑ TREATMENT INDICATION
- ☐ INITIAL ASSESSMENT

[UPDATE]

▼ MEDICATIONS
 MEDICATION REGIMEN                    2 OF 2
 MEDICATION ADHERENCE                  1 OF 1
 MEDICATION ADHERENCE BARRIERS
 GUIDELINE MEDICATIONS                 6 OF 6

☐ KEY MEDS PRESCRIBED:

| DESCRIPTION | YES | NO | OPTIONAL | CONTRAINDICATED |
|---|---|---|---|---|
| DAILY ASPIRIN | ☐ ⦿ | | | |
| ANTIPLATELET (OTHER THAN ASA) | | ⦿ | ☐ | ☐ |
| ☐ ACE INHIBITOR - CAD, DIA | ⦿ | | ☐ | ☐ |
| BETA BLOCKER - CAD, DIA | | ○ | ☐ | ○ |
| ☐ LIPID-LOWERING AGENT | ⦿ | | ☐ | ☐ |
| INHALED SHORT-ACTING BETA2-AGONIST-ASTHMA | | | ☐ | ⦿ |

REMINDERS

NO REMINDERS

[NEW...]

CALL NOTES

[SPELL]

[DONE]

POPULATION CARE MANAGEMENT

McKESSON
*EMPOWERING HEALTHCARE*
*POPULATION CARE MANAGEMENT*

JANE DOE, 39 YEARS OLD.
BELONGS TO MY TEST CLIENT.

CALL TIME: 00:02:08
CALL TYPE: INITIAL ASSESSMENT
RISK: 3
PRODUCT: CHRONIC CARE MANAGEMENT
DATE ENROLLED: 06/09/2009

[ MAP ] [ DEMOGRAPHICS ] [ MEDICATION ] [ UTILIZATION ] [ CARE COORDINATION ] [ ALERTS ] [ PROVIDERS ] [ END CONTACT ] [ CANCEL ]
HISTORY

CALL ACTIVITIES
- ☑ INTRODUCTION
- ☑ MEDICAL HISTORY
- ☑ TREATMENT INDICATION
- ⚠ INITIAL ASSESSMENT

[ UPDATE ]

▼ SELF MANAGEMENT
- IMMUNIZATIONS ........................ 0 OF 2
- TOBACCO ................................ 0 OF 1
- ALCOHOL/SUBSTANCE ABUSE ........... 1 OF 2
- PHYSICAL ACTIVITY ..................... 0 OF 1
- NUTRITION .............................. 0 OF 2
- SELF CONDITION MANAGEMENT

SELF MANAGEMENT INCLUDES:
- ☑ PERFORMS FOOT SELF-CARE
- ☑ MONITORS BLOOD GLUCOSE AS DIRECTED
- ☑ UNDERSTANDS DIABETIC NUTRITION RECOMMENDATIONS
- ☑ UNDERSTANDS EFFECTS OF PHYSICAL ACTIVITY ON BLOOD GLUCOSE — 1302
- ☑ UNDERSTANDS CAD NUTRITION RECOMMENDATIONS — 1304
- ☑ UNDERSTANDS ANGINA SYMPTOM/TREATMENT RECOMMENDATIONS
- ☑ HAS A WRITTEN ASTHMA ACTION PLAN
- ☑ IDENTIFIES AND AVOIDS EXPOSURE TO TRIGGERS — 306
- ☐ AVOIDS SECONDHAND SMOKE
- ☐ NONE OF THE ABOVE

MONITORS PEAK FLOW AS DIRECTED
- ● YES
- ○ NO
- ○ NO PEAK FLOW METER MONITORING PRESCRIBED

REMINDERS

NO REMINDERS

[ NEW... ]

CALL NOTES
[ SPELL ]

[ DONE ]

POPULATION CARE MANAGEMENT

McKESSON
*EMPOWERING HEALTHCARE*
*POPULATION CARE MANAGEMENT*

| MAP | DEMOGRAPHICS | MEDICATION | UTILIZATION | CARE COORDINATION | ALERTS | PROVIDERS | END CONTACT | CANCEL |

JANE DOE 39 YEARS OLD.
BELONGS TO MY TEST CLIENT.
HISTORY

CALL TIME: 00:07:50
CALL TYPE: INITIAL ASSESSMENT
RISK: 1
PRODUCT: CHRONIC CARE MANAGEMENT
DATE ENROLLED: 06/09/2009

REMINDERS

NO REMINDERS

[NEW...]

CALL NOTES

[SPELL]

HISTORY

ALERTS

LAB/BIOMETRIC ALERTS — 0 OF 3
BLOOD PRESSURE (OBTAINED OUTSIDE MD OFFICE)
☐ YES
DESCRIPTOR/S:
    SBP GREATER THAN 180 mmHg IN PAST 2 DAYS AND HAS SEVERE HEADACHE
    SBP GREATER THAN 180 mmHg IN PAST 2 DAYS
    SBP LESS THAN 90 mmHg IN PAST 2 DAYS
    DBP GREATER THAN 110 mmHg IN PAST 2 DAYS
FASTING BLOOD SUGAR (OBTAINED OUTSIDE MD OFFICE):
☐ YES
DESCRIPTOR/S:
    GREATER THAN 400 mg/dL (22 mmol/l) WITHIN LAST 24 HOURS
    GREATER THAN 250 mg/dL (13.8 mmol/l) ON 2 OR MORE OCCASIONS IN PAST WEEK
    LESS THAN 60 mg/dL (3.3 mmol/l) on 2 OR MORE OCCASIONS IN PAST WEEK
RECENT PEAK FLOW METER READING
☐ YES
DESCRIPTOR/S:
    PEAK FLOW READINGS ARE WORSENING IN SPITE OF RESCUE INHALER
    RED ZONE, CURRENTLY
    RED ZONE, WITHIN LAST 24-48 HOURS, BUT NOT CURRENTLY
    YELLOW ZONE, CURRENTLY
    YELLOW ZONE, WITHIN LAST 24-48 HOURS, BUT NOT CURRENTLY

| | OPTIONAL |
|---|---|
| MEDICATION ALERTS | 0 OF 2 |
| MENTAL/BEHAVIORAL HEALTH ALERTS | 0 OF 1 |
| CHEST DISCOMFORT ALERTS | 0 OF 2 |
| CNS ALERTS | 0 OF 4 |
| RESPIRATORY ALERTS | 0 OF 5 |
| SYMPTOM ALERTS | |

DONE

| SCREENING TOOL -- WEB PAGE DIALOG | | | | |
|---|---|---|---|---|
| OVER THE LAST 2 WEEKS, HOW OFTEN HAVE YOU BEEN BOTHERED BY ANY OF THE FOLLOWING PROBLEMS? | | | | |
| DESCRIPTION | NOT AT ALL | SEVERAL DAYS | MORE THAN HALF THE DAYS | NEARLY EVERY DAY |
| LITTLE INTEREST OR PLEASURE IN DOING THINGS *NEARLY EVERY DAY, 06/10/2009* | ○ | ○ | ○ | ○ |
| FEELING DOWN, DEPRESSED, OR HOPELESS *NEARLY EVERY DAY, 06/10/2009* | ○ | ○ | ○ | ○ |
| TROUBLE FALLING/STAYING ASLEEP, SLEEPING TOO MUCH | ○ | ○ | ○ | ○ |
| FEELING TIRED OR HAVING LITTLE ENERGY | ○ | ○ | ○ | ○ |
| POOR APPETITE OR OVEREATING | ○ | ○ | ○ | ○ |
| FEELING BAD ABOUT YOURSELF - OR THAT YOU ARE A FAILURE OR HAVE LET YOURSELF OR YOUR FAMILY DOWN | ○ | ○ | ○ | ○ |
| TROUBLE CONCENTRATING ON THINGS, SUCH AS READING THE NEWSPAPER OR WATCHING TELEVISION | ○ | ○ | ○ | ○ |
| MOVING OR SPEAKING SO SLOWLY THAT OTHER PEOPLE COULD HAVE NOTICED. OR THE OPPOSITE-- BEING SO FIDGETY OR RESTLESS THAT YOU HAVE BEEN MOVING AROUND A LOT MORE THAN USUAL. | ○ | ○ | ⊙ | ○ |
| THOUGHTS THAT YOU WOULD BE BETTER OFF DEAD OR OF HURTING YOURSELF IN SOME WAY | ○ | 🛈 ○ | 🛈 ○ | 🛈 ⊙ |

HOW DIFFICULT HAVE THESE PROBLEMS MADE IT FOR YOU TO DO YOUR WORK, TAKE CARE OF THINGS AT HOME, OR GET ALONG WITH OTHER PEOPLE?
  ○ NOT DIFFICULT AT ALL
  ○ SOMEWHAT DIFFICULT
  ○ VERY DIFFICULT
  ○ EXTREMELY DIFFICULT

🛈 PHQ-9
  [18] [CALCULATE]

PERMISSION TO SHARE DEPRESSION SCREEN RESULTS WITH (SELECT ALL THAT APPLY)  *MEMBER DOES NOT GIVE PERMISSION TO SHARE DEPRESSION SCREEN, 06/10/2009*
  ☐ YOUR PROVIDER
  ☐ YOUR HEALTH PLAN
  ☐ MEMBER DOES NOT GIVE PERMISSION TO SHARE DEPRESSION SCREEN

PATIENT HEALTH QUESTIONNAIRE -- PHQ-9
DEVELOPED BY DRS. ROBERT L. SPLITZER, JANET B.W. WILLIAMS, KURT KROENKE AND COLLEAGUES, WITH AN EDUCATIONAL GRANT FROM PFIZER INC.
COPYRIGHT 2005 PFIZER, INC. ALL RIGHTS RESERVED. REPRODUCED WITH PERMISSION.

[DONE]

POPULATION CARE MANAGEMENT

McKESSON
*EMPOWERING HEALTHCARE*
POPULATION CARE MANAGEMENT

MAP | DEMOGRAPHICS | MEDICATION | UTILIZATION | CARE COORDINATION | ALERTS | PROVIDERS | END CONTACT | CANCEL

JANE DOE, 39 YEARS OLD.
BELONGS TO MY TEST CLIENT.
HISTORY

CALL TIME: 00:09:33
CALL TYPE: INITIAL ASSESSMENT
PRODUCT: CHRONIC CARE MANAGEMENT
DATE ENROLLED: 06/09/2009

CALL INFORMATION | COMMUNICATIONS | SUMMARY POINTS | COMPLETION SURVEY

SUMMARY POINTS HAVE NOT BEEN ANSWERED.
CLINICAL CRITERION
- ☐ ○ TWO OR GREATER HOSPITALIZATIONS IN 60 DAYS. HIGH RISK FOR READMIT
- ☐ ○ NEEDS ACTIVE CARE COORDINATION
- ☐ ○ COMPLICATED SEVERE MEDICAL
- ☐ ○ FORWARD MEMBER TO CTI
- ☐ ○ EXPERIENCING SIGNIFICANT DISEASE-RELATED SYMPTOMS
- ☐ ○ MULTIPLE PROVIDERS WHO DO NOT COMMUNICATE
- ☐ ○ RECENT TERMINAL PROGNOSIS/DIAGNOSIS

OPERATIONAL CRITERION
- ○ FORWARD TO CLIENT
- ○ FORWARD TO PARTNER
- ○ HEALTH PLAN REQUEST
- ○ INVALID PHONE
- ○ MEDICAL EXCLUSIONS
- ○ MEMBER REFUSES PARTICIPATION
- ○ MEMBER HAS EXPIRED
- ○ MEMBER REQUEST
- ○ PENDING CONTRACT
- ○ SKILLED NURSING FACILITY
- ○ UNABLE TO LOCATE MEMBER
- ○ WRONG ADDRESS
- ○ OTHER

REMINDERS

NO REMINDERS

NEW...

CALL NOTES
SPELL

HISTORY

END CALL

COPYRIGHT©2009 MCKESSON HEALTH SOLUTIONS LLC, ALL RIGHTS RESERVED

DONE

FIG. 28

METHODS, APPARATUSES, AND COMPUTER PROGRAM PRODUCTS FOR FACILITATING CO-MORBID CARE MANAGEMENT

TECHNOLOGICAL FIELD

Embodiments of the present invention relate generally to health promotion and, more particularly, relate to methods, apparatuses, and computer program products for facilitating co-morbid care management.

BACKGROUND

Factors such as rising treatment costs and an aging population are contributing to rapidly rising health care costs. These rising costs may be burdensome to both individuals and payers (e.g., private and government funded insurance providers). Some efforts have thus been made to reduce health care costs associated with treating an individual through use of disease and care management programs. However, the disease and care management programs that have been implemented to date are often condition-centric and may fail to adequately address all of an individual's issues in an effective manner to promote the individual's health and wellbeing while also reducing the health care costs associated with the individual.

BRIEF SUMMARY OF SOME EXAMPLES OF THE INVENTION

Methods, apparatuses, and computer program products are therefore provided for facilitating co-morbid care management. In this regard, methods, apparatuses, and computer program products are provided that may provide several advantages to payers and members of care management plans. Embodiments of the invention provide for a care management program that is member-centric in that assessment and coaching is customized based on multiple medical conditions affecting a member enrolled in a care management plan. According to some embodiments of the invention, a plurality of medical conditions affecting a member are determined and then a blended co-morbid assessment question set is generated based on the determined plurality of medical conditions such that a single assessment question set is generated that is member-specific and concurrently addresses multiple medical conditions affecting the member. Accordingly, the member may be spared from redundant questioning that may occur if separate condition-specific assessment question sets were used to separately assess the member with respect to each medical condition affecting the member. Some embodiments of the invention wherein a blended co-morbid assessment question set is generated further ensure that only assessment questions that are appropriate given the mix of medical conditions affecting the member are included in the co-morbid assessment question set. Accordingly, if coaching is given to a member based on responses to assessment questions in the blended co-morbid assessment question set, the member may be spared being given conflicting advice or advice targeted to one medical condition affecting the member that may be inappropriate given a second medical condition affecting the member.

Some embodiments of the invention further provide for generation of a member activity plan based at least in part on member responses to assessment questions in the blended co-morbid assessment question set. Such embodiments enable tailored coaching of the member to address factors that may be affecting the member's health in view of the member's existing medical conditions, risk factors, and/or responses to assessment questions. Some embodiments provide for generation of the member activity plan in real time as member responses to assessment questions in the blended co-morbid assessment question set are determined so that a nurse-coach assessing and coaching the member may provide coaching to the member prior to completion of all of the assessment questions in the blended co-morbid assessment question set. Such embodiments may facilitate a more conversational assessment-coaching session so that a member may derive some benefit earlier in the session and remain more engaged during the duration of the assessment-coaching session than the member might if the member had to answer every assessment question prior to receiving any coaching.

In a first example embodiment, a method for facilitating co-morbid care management is provided. The method of this embodiment comprises determining a plurality of medical conditions affecting a member enrolled in a care management plan. The method of this embodiment further comprises activating, based at least in part upon the determined medical conditions, a plurality of member assessment modules. Each activated member assessment module of this embodiment is associated with a respective determined medical condition. Each activated member assessment module of this embodiment also comprises a set of assessment questions targeted to the medical condition with which the member assessment module is associated. The method of this embodiment additionally comprises generating a blended co-morbid assessment question set based at least in part on the assessment question sets of the activated member assessment modules by blending the assessment question sets of the activated member assessment modules into a blended co-morbid assessment question set.

In another example embodiment, an apparatus for facilitating co-morbid care management is provided. The apparatus of this embodiment comprises a processor configured to cause the apparatus to determine a plurality of medical conditions affecting a member enrolled in a care management plan. The processor of this embodiment is further configured to cause the apparatus to activate, based at least in part upon the determined medical conditions, a plurality of member assessment modules. Each activated member assessment module of this embodiment is associated with a respective determined medical condition. Each activated member assessment module of this embodiment also comprises a set of assessment questions targeted to the medical condition with which the member assessment module is associated. The processor of this embodiment is additionally configured to cause the apparatus to generate a blended co-morbid assessment question set based at least in part on the assessment question sets of the activated member assessment modules by blending the assessment question sets of the activated member assessment modules into a blended co-morbid assessment question set.

In another example embodiment, a computer program product for facilitating co-morbid care management is provided. The computer program product of this embodiment includes at least one computer-readable storage medium having computer-readable program instructions stored therein. The computer program product of this embodiment comprises program instructions configured for determining a plurality of medical conditions affecting a member enrolled in a care management plan. The computer program product of this embodiment further comprises program instructions configured for activating, based at least in part upon the determined medical conditions, a plurality of member assessment modules. Each activated member assessment module of this embodiment is associated with a respective determined medical condition. Each activated member assessment module of this embodiment also comprises a set of assessment questions targeted to the medical condition with which the member assessment module is associated. The computer program product of this embodiment additionally comprises program instructions configured for generating a blended co-morbid assessment question set based at least in part on the assessment question sets of the activated member assessment modules by blending the assessment question sets of the activated member assessment modules into a blended co-morbid assessment question set.

In another example embodiment, an apparatus for facilitating co-morbid care management is provided. The apparatus of this embodiment comprises means for determining a plurality of medical conditions affecting a member enrolled in a care management plan. The apparatus of this embodiment further comprises means for activating, based at least in part upon the determined medical conditions, a plurality of member assessment modules. Each activated member assessment module of this embodiment is associated with a respective determined medical condition. Each activated member assessment module of this embodiment also comprises a set of assessment questions targeted to the medical condition with which the member assessment module is associated. The apparatus of this embodiment additionally comprises means for generating a blended co-morbid assessment question set based at least in part on the assessment question sets of the activated member assessment modules by blending the assessment question sets of the activated member assessment modules into a blended co-morbid assessment question set.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the invention in any way. It will be appreciated that the scope of the invention encompasses many potential embodiments, some of which will be further described below, in addition to those here summarized.

BRIEF DESCRIPTION OF THE DRAWING(S)

Having thus described embodiments of the invention in general terms, reference will now be made to the accompanying drawings, which are not necessarily drawn to scale, and wherein:

FIGS. 4-28 illustrate screenshots of a graphical user interface for facilitating co-morbid care management according to an exemplary embodiment of the invention.

DETAILED DESCRIPTION

Figure 1:
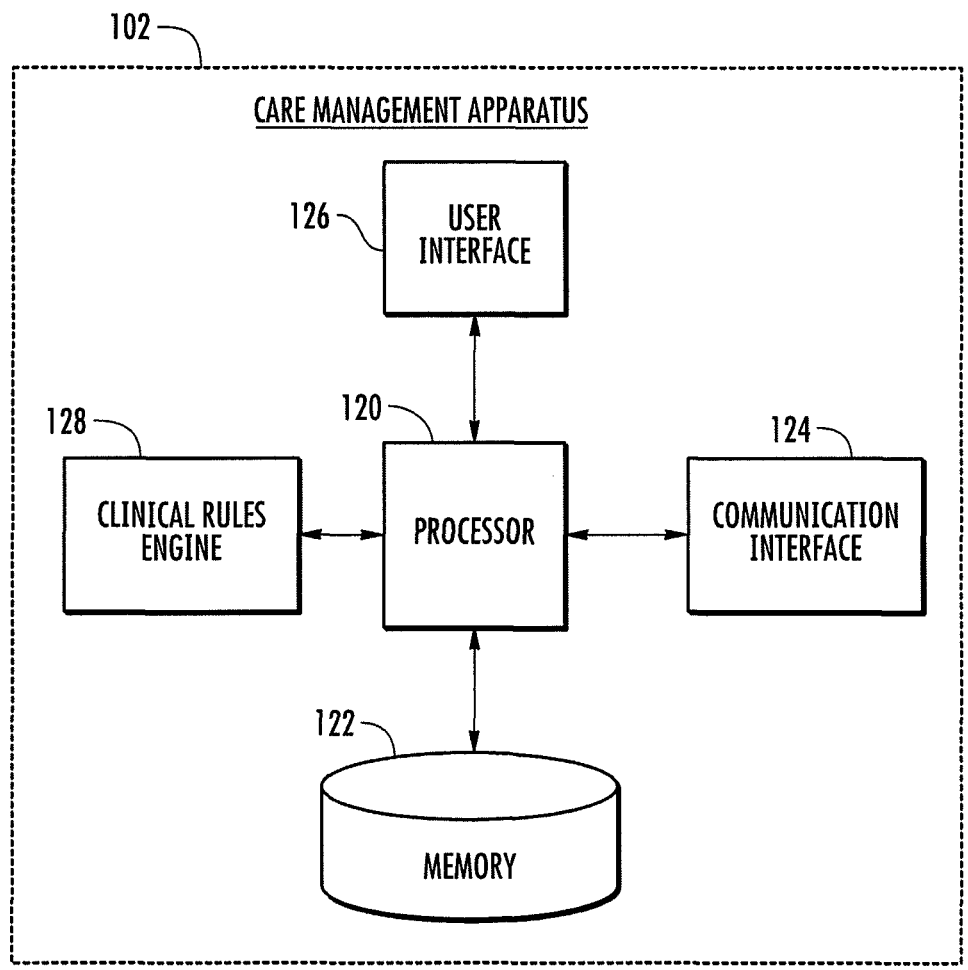
FIG. 1 illustrates an apparatus for facilitating co-morbid care management according to an exemplary embodiment of the present invention.

Some embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like reference numerals refer to like elements throughout.

FIG. 1 illustrates a care management apparatus 102 for facilitating co-morbid care management according to an exemplary embodiment of the present invention. As used herein, "exemplary" merely means an example and as such represents one example embodiment for the invention and should not be construed to narrow the scope or spirit of the invention in any way. It will be appreciated that the scope of the invention encompasses many potential embodiments in addition to those illustrated and described herein. As such, while FIG. 1 illustrates one example of a configuration of a care management apparatus for facilitating co-morbid care management, numerous other configurations may also be used to implement embodiments of the present invention.

The care management apparatus 102 may be embodied as a server, desktop computer, laptop computer, mobile terminal, mobile computer, mobile phone, mobile communication device, audio/video player, television device, network node, multiple computing devices in communication with each other, any combination thereof, and/or the like. In an exemplary embodiment the care management apparatus 102 includes various means, such as a processor 120, memory 122, communication interface 124, user interface 126, and clinical rules engine 128 for performing the various functions herein described. These means of the care management apparatus 102 as described herein may be embodied as, for example, circuitry, hardware elements (e.g., a suitably programmed processor, combinational logic circuit, and/or the like), a computer program product comprising computer-readable program instructions (e.g., software or firmware) stored on a computer-readable medium (e.g. memory 122) that is executable by a suitably configured processing device (e.g., the processor 120), or some combination thereof.

The processor 120 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an ASIC (application specific integrated circuit) or FPGA (field programmable gate array), or some combination thereof. Accordingly, although illustrated in FIG. 1 as a single processor, in some embodiments the processor 120 comprises a plurality of processors. The plurality of processors may be embodied on a single computing device or may be distributed across a plurality of computing devices collectively configured to function as the care management apparatus 102. The plurality of processors may be in operative communication with each other and may be collectively configured to perform one or more functionalities of the care management apparatus 102 as described herein. In an exemplary embodiment, the processor 120 is configured to execute instructions stored in the memory 122 or otherwise accessible to the processor 120. These instructions, when executed by the processor 120, may cause the care management apparatus 102 to perform one or more of the functionalities of the care management apparatus 102 as described herein. As such, whether configured by hardware or software methods, or by a combination thereof, the processor 120 may comprise an entity capable of performing operations according to embodiments of the present invention while configured accordingly. Thus, for example, when the processor 120 is embodied as an ASIC, FPGA or the like, the processor 120 may comprise specifically configured hardware for conducting one or more operations described herein. Alternatively, as another example, when the processor 120 is embodied as an executor of instructions, such as may be stored in the memory 122, the instructions may specifically configure the processor 120 to perform one or more algorithms and operations described herein.

The memory 122 may include, for example, volatile and/or non-volatile memory. Although illustrated in FIG. 1 as a single memory, the memory 122 may comprise a plurality of memories. The plurality of memories may be embodied on a single computing device or distributed across a plurality of computing devices. The memory 122 may comprise volatile memory, non-volatile memory, or some combination thereof. In this regard, the memory 122 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof. The memory 122 may be configured to store information, data, applications, instructions, or the like for enabling the care management apparatus 102 to carry out various functions in accordance with exemplary embodiments of the present invention. For example, in at least some embodiments, the memory 122 is configured to buffer input data for processing by the processor 120. Additionally or alternatively, in at least some embodiments, the memory 122 is configured to store program instructions for execution by the processor 120. The memory 122 may store information in the form of static and/or dynamic information. This stored information may be stored and/or used by the clinical rules engine 128 during the course of performing its functionalities.

The communication interface 124 may be embodied as any device or means embodied in circuitry, hardware, a computer program product comprising computer readable program instructions stored on a computer readable medium (e.g., the memory 122) and executed by a processing device (e.g., the processor 120), or a combination thereof that is configured to receive and/or transmit data from/to another device, such as, for example, a server, a user terminal (e.g., the user terminal 208 illustrated in FIG. 2), a data source (e.g., the data source 206 illustrated in FIG. 2), and/or the like. In some embodiments, aspects of the communication interface 126 may be reduced or even eliminated. In at least one embodiment, the communication interface 124 is at least partially embodied as or otherwise controlled by the processor 120. In this regard, the communication interface 124 may be in communication with the processor 120, such as via a bus. The communication interface 124 may include, for example, an antenna, a transmitter, a receiver, a transceiver, network interface card, and/or supporting hardware or software for enabling communications with another computing device. The communication interface 124 may be configured to receive and/or transmit data using any protocol that may be used for communications between computing devices. The communication interface 124 may additionally be in communication with the memory 122, user interface 126, and/or clinical rules engine 128, such as via a bus.

The user interface 126 may be in communication with the processor 120 to receive an indication of a user input and/or to provide an audible, visual, mechanical, or other output to a user. As such, the user interface 126 may include, for example, a keyboard, a mouse, a joystick, a display, a touch screen display, a microphone, a speaker, and/or other input/output mechanisms. In embodiments wherein the care management apparatus 102 is embodied as a server, aspects of the user interface 126 may be reduced or the user interface 126 may even be eliminated. Alternatively, such as in embodiments wherein the care management apparatus 102 is embodied as a server, at least some aspects of the user interface 126 may be embodied on an apparatus used by a user that is in communication with the care management apparatus 102, such as for example, the user terminal 208 illustrated in FIG. 2. The user interface 126 may be in communication with the memory 122, communication interface 124, and/or clinical rules engine 128, such as via a bus.

The clinical rules engine 128 may be embodied as various means, such as circuitry, hardware, a computer program product comprising computer readable program instructions stored on a computer readable medium (e.g., the memory 122) and executed by a processing device (e.g., the processor 120), or some combination thereof and, in one embodiment, is embodied as or otherwise controlled by the processor 120. In embodiments wherein the clinical rules engine 128 is embodied separately from the processor 120, the clinical rules engine 128 may be in communication with the processor 120. The clinical rules engine 128 may further be in communication with one or more of the memory 122, communication interface 124, or user interface 126, such as via a bus.

Figure 2:
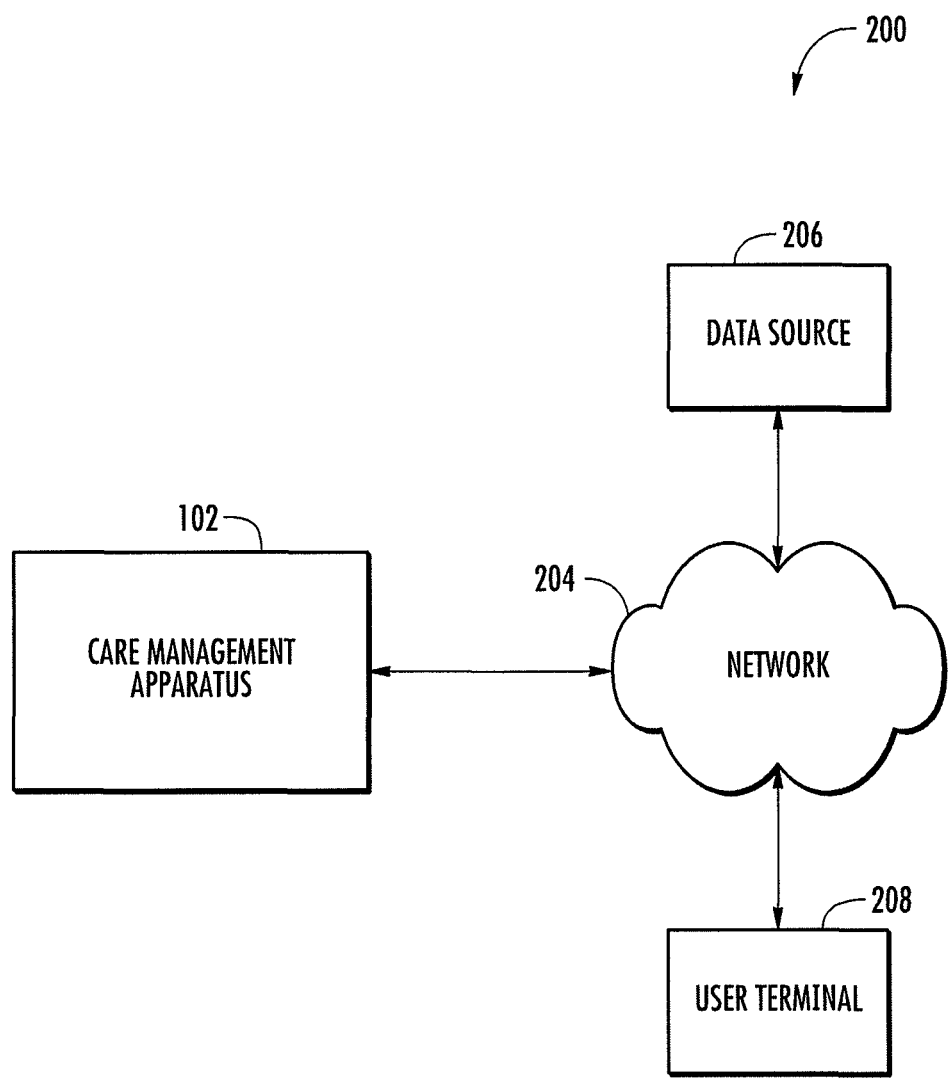
FIG. 2 illustrates a system for facilitating co-morbid care management according to an exemplary embodiment of the present invention.

FIG. 2 illustrates a system 200 for facilitating co-morbid care management according to an exemplary embodiment of the present invention. In this regard, FIG. 2 illustrates a system wherein the care management apparatus 102 comprises and/or is embodied as a node on a network 204. The network 204 may comprise a wireless network (e.g., a cellular network, wireless local area network, wireless personal area network, wireless metropolitan area network, and/or the like), a wireline network, or some combination thereof, and in some embodiments comprises the internet.

The system 200 may comprise one or more data sources 206 in communication with the care management apparatus 102 to facilitate access by the care management apparatus 102 to remotely stored medical data, patient/member demographic data, and/or the like. The data source 206 may comprise, for example, a network attached storage device, a server, a desktop computer, laptop computer, mobile terminal, mobile computer, mobile phone, mobile communication device, audio/video player, any combination thereof, and/or the like. A data source may be maintained by a payer (e.g., insurer), medical services provider, clinic, hospital, doctor's office, and/or the like, and may store member insurance claims information, patient/member health history, electronic medical records, and/or the like. It will be appreciated that when the clinical rules engine 128 is described herein to access medical data, member data, and/or other data or information from the memory 122, accessing data from the memory 122 is provided merely for purposes of example and the clinical rules engine 128 may be configured to access data from the memory 122 and/or from a data source(s) 206 over the network 204.

The system 200 may additionally or alternatively comprise one or more user terminals 208. In this regard, in embodiments wherein the care management apparatus 102 comprises one or more servers, the one or more servers may be in communication with one or more remote user terminals 206 over the network 204 to facilitate a user of a user terminal 208 to remotely access at least some of the functionality provided by the care management apparatus 102 in accordance with embodiments of the invention. Such an arrangement may allow multiple users at multiple user terminals 208 to concurrently access functionality provided by the care management apparatus 102. A user terminal 208 may comprise any device configured for use by a user to access co-morbid care management services provided by the care management apparatus 102 over the network 204. In this regard, a user terminal 208 may be embodied as a desktop computer, laptop computer, mobile terminal, mobile computer, mobile phone, mobile communication device, audio/video player, television device, any combination thereof, and/or the like.

In embodiments, wherein a user terminal 208 is used to access co-morbid care management services provided by the care management apparatus 102, elements of the care management apparatus 102 that were described with respect to FIG. 1 and functionality attributed thereto may be distributed between the care management apparatus 102 and user terminal 208. For example, the clinical rules engine 128 may be distributed between the care management apparatus 102 and user terminal 208, such that functionality attributed to the clinical rules engine 128 may be performed by the care management apparatus 102 and/or by the user terminal 208. Additionally or alternatively, where the clinical rules engine 128 is said to cause a graphical user interface, data, and/or the like to be displayed, it will be appreciated that the clinical rules engine 128 may be configured to cause the graphical user interface, data, and/or the like to be displayed on a display coupled to the care management apparatus 102 and/or may be configured to cause transmission of the data to be displayed via the communication interface 124 to a user terminal 208 such that the graphical user interface, data, and/or the like may be displayed on a display coupled to the user terminal 208. Similarly, where receipt of a selection of a response to an assessment question and/or receipt of other user input is described, it will be appreciated that the user may be providing the selection or input via the user interface 126 and/or may be interacting with a user terminal 208 such that the input and/or selection is transmitted from the user terminal 208 to the care management apparatus 102, where it may be received by the communication interface 124 and/or clinical rules engine 128. Further, program instructions, data, and/or the like said to be stored in the memory 122 may be stored at the care management apparatus 102 and/or may be stored on a user terminal 208.

In some embodiments, the clinical rules engine 128 is configured to determine medical conditions affecting a member enrolled in a care management plan. This determination may take place prior to, concurrent with, and/or after enrollment of the member in the care management plan. The care management plan may, for example, be administered and/or contracted by a health care payer (e.g., insurer) to manage and promote health of members covered by the payer in an effort to reduce health care costs incurred by the payer due to coverage of the members.

The clinical rules engine 128 may be configured to analyze any information available to the clinical rules engine 128 in order to determine medical conditions affecting the member. This information may be stored on the memory 122 and/or by one or more data sources 106. Information analyzed by the clinical rules engine 128 may include, for example, claims information detailing claims filed by and/or on behalf of the member, predictive modeling inputs (e.g., based on the member's medical history, family medical history, age, sex, location, environmental factors, demographic data, and/or the like), electronic medical records for the member, client data, partner data, payer data, other available member medical data, and/or the like. Additionally or alternatively, the clinical rules engine 128 may be configured to determine medical conditions affecting the member by receiving one or more indications of medical conditions affecting the member from a data source 106 and identifying the indicated medical conditions. In this regard, a data source 106 may be configured to determine medical conditions affecting a member and to provide an indication of the determined medical condition(s) to the care management apparatus 102. The clinical rules engine 128 may be configured to determine a medical condition affecting a member based on user input, such as by a nurse coach interacting with the member. Although referred to as a nurse coach, the nurse coach may not necessarily be a registered nurse, and may be any individual having appropriate training that is utilizing embodiments of the invention to assess and/or coach a member. Accordingly, a nurse coach may determine a medical condition affecting a member during a conversation with the member.

The clinical rules engine 128 may be further configured to prioritize assessment modules based on a driver score for a determined medical condition affecting a member that describes a total cost and/or risk contribution of that medical condition to the member's health. In this regard, the clinical rules engine 128 may be configured to determine a driver score for a determined medical condition by calculating the driver score based on available data and/or may be configured to determine a driver score based on an indication received from a data source 106, which may have calculated the driver score. The clinical rules engine 128 may also be configured to update the determined medical conditions affecting a member and/or calculated driver scores for a determined medical condition (e.g., periodically) (e.g., by determining updates from available data and/or based on indications received from a data source(s) 106).

The clinical rules engine 128 may store determined medical conditions and/or driver scores associated therewith in the memory 122. Accordingly, the clinical rules engine 128 may be configured to determine medical conditions affecting a member enrolled in a care management plan by accessing the memory 122 to determine medical conditions previously determined to be affecting the member.

After medical conditions affecting a member have been determined, the clinical rules engine 128 is configured in some embodiments to activate, based at least in part upon determined medical conditions, one or more member assessment modules. In this regard, a member assessment module is associated with a medical condition and includes a set of assessment questions targeted to the medical condition with which the member assessment module is associated. Accordingly, the clinical rules engine 128 may be configured to access and activate member assessment modules associated with medical conditions determined to be affecting the member. In this regard, the a plurality of predefined member assessment modules, each associated with a specific medical condition, may be stored in the memory 122 so that the clinical rules engine 128 may access and activate specific member assessment modules associated with medical conditions affecting a member to facilitate creation of a member-centric care management assessment and plan tailored to and addressing the combination of medical conditions uniquely affecting the member.

In some embodiments, a nurse coach may select member assessment modules for activation by the clinical rules engine 128. In this regard, a nurse coach may identify in a conversation with a member which of the medical conditions affecting the member the member wishes to work on and may then provide user input indicating which member assessment modules should be activated by the clinical rules engine 128.

When multiple member assessment modules have been activated for a member, the clinical rules engine 128 may be configured to generate a blended co-morbid assessment question set based at least in part on the assessment question sets of the activated member assessment modules by blending the assessment question sets of the activated member assessment modules into a blended co-morbid assessment question set. In this regard, a blended co-morbid assessment question set in accordance with some embodiments of the invention comprises a blended set of assessment questions being targeted to a range of medical conditions determined to be affecting the member for which corresponding member assessment modules were activated. The blended set facilitates a comprehensive assessment of the member rather than a condition-centric siloed approach by which the member would be assessed separately with respect to each medical condition affecting the member.

In some embodiments, the clinical rules engine 128 is configured to blend the assessment question sets of the activated member assessment modules into a blended co-morbid assessment question set at least in part by eliminating a duplicate assessment question when an assessment question is included in more than one of the assessment question sets of the activated member assessment modules so that the blended co-morbid assessment question set comprises a set of unique assessment questions.

Additionally or alternatively, the clinical rules engine 128 may be configured to ensure that the blended co-morbid assessment question set does not comprise conflicting or medically inappropriate assessment questions. Accordingly, the clinical rules engine 128 may be configured to determine whether the assessment question sets of the activated member assessment modules collectively comprise a group of two or more conflicting assessment questions. When the assessment question sets of the activated member assessment modules are determined to comprise a group of conflicting assessment questions, the clinical rules engine 128 may be configured to determine which assessment question in the group of conflicting assessment questions is appropriate to all of the determined medical conditions and/or other pertinent clinical or behavioral information and include that assessment question in the blended co-morbid assessment question set while discarding the remaining assessment question(s) in the group of conflicting assessment questions.

The clinical rules engine 128 may also be configured to track multiple differing clinical targets for a plurality of conditions that utilize the same clinical metric such as, for example, varying blood pressure values for members with no conditions, with diabetes or members with diabetes and coronary artery disease. For example, a member may be affected by diabetes and heart disease, for which first and second member assessment modules have been activated. The first activated member assessment module may comprise a set of assessment questions targeted to diabetes and the second member assessment module may comprise a set of assessment questions targeted to coronary artery disease. However, one or more of the assessment questions in the set targeting diabetes and thus may conflict with one or more assessment questions in the set targeting coronary artery disease. For example, there may be different optimum targeted blood pressure levels for diabetes patients and coronary artery disease patients. Accordingly, an assessment question framed in terms of an optimum blood pressure target level for a diabetic may conflict with an assessment question framed in terms of an optimum blood pressure target level for a patient having coronary artery disease. The clinical rules engine 128 may be configured to determine the existence of the group of conflicting blood pressure questions and in response to determine the assessment question that is framed in terms of an optimum blood pressure target level that is medically appropriate for a member having both diabetes and coronary artery disease and include that assessment question in the blended co-morbid assessment question set. Furthermore, the clinical rules engine 128 may be configured to track multiple targets for the member to those differing goals values for the same metrics (example for illustrative purposes only: BP for Diabetic <=140/90 and BP for CAD <120/80). In another example, the assessment question set targeted to diabetes may include an assessment question(s) about whether the member is taking one or more medications known to be clinically appropriate for treatment of diabetes. However, one of those medications may be on inappropriate for administration to a person having heart disease. Accordingly, the clinical rules engine 128 may be configured to determine the conflict and ensure that the blended co-morbid assessment question set does not include an assessment question inquiring whether the member is taking a medication that is inappropriate given his heart disease by discarding and/or modifying the assessment question. The clinical rules engine 128 may additionally be configured to modify the assessment question's associated clinical metrics/targets to be tracked over time to demonstrate member progress. For example, if the member has a first and second medical condition, each having a different target metric for a parameter, such as blood pressure, the clinical rules engine 128 may be configured to include both target metrics in the assessment question set. In this regard, although ideally the member should meet the most stringent target metric, the clinical rules engine 128 may configure the assessment question set to facilitate determining compliance per condition and also to monitor the member's progress over time toward meeting the target metrics.

In generating the blended co-morbid assessment question set, the clinical rules engine 128 may be further configured to develop, access, and/or analyze treatment indications. Treatment indications capture condition specific medical history and details such as, for example, a history of medical procedures undergone by the member, medical events encountered by the member, exacerbations encountered by the member, and/or the like. For example, a cardiac member who has recently had a stint implanted may have a different clinically recommended medication regimen than a cardiac member who has not undergone a stint implantation. The clinical rules engine 128 may be configured to utilize treatment indications to generate the blended co-morbid assessment question set and targets such as biometric values, required tests and guideline medications in accordance with predefined rules, such as may be defined by the activated member assessment modules.

In an exemplary embodiment, the clinical rules engine 128 is configured to include a set of barriers and common care assessment questions in the generated blended co-morbid assessment question set. The set of barriers and common care assessment questions may be used to assess a member regardless of the medical conditions affecting a member and may be used to assess even a member that is not affected by any medical conditions. The set of barriers and common care assessment questions may be addressed prior to addressing any assessment questions targeted to a medical condition. In this regard, the barriers and common care assessment question set may comprise a funnel through which all members are assessed to determine problems that should be addressed prior to addressing any condition-specific problems. Barriers and common care assessment questions may include, for example, assessment questions regarding a member's resources (e.g., whether member has adequate living conditions, food, support system, transportation, and/or the like), medical home (e.g., whether member has a primary care physician), medications taken by the member, lab values/metrics of the member, self management by the member (e.g., immunizations, tobacco usage, alcohol/substance abuse, physical activity level, nutrition, and/or the like), and/or the like. Issues addressed by barrier and common assessment questions may thus be known to impact a member's health regardless of any medical condition affecting the member's health.

Once the blended co-morbid assessment question set is generated by the clinical rules engine 128, the clinical rules engine 128 may be configured to cause a graphical user interface through which the assessment questions of the blended co-morbid assessment set may be viewed by a nurse coach. The nurse coach may then carry on a conversation with the member (e.g., over the phone, in person, via a text-based chat system, and/or the like) and carry out an assessment of the member based on the blended co-morbid assessment question set. In this regard, the blended co-morbid assessment question set may provide a single topic of discussion for the nurse coach and member to cover that captures all related items for all of the conditions the member and nurse coach have chosen to manage as well as barriers and common care items that are relevant for all members regardless of their medical history.

The nurse coach may enter an indication of member responses to assessment questions via the user interface 126 and the clinical rules engine 128 may then determine one or more member responses to the assessment questions from entered indications. The clinical rules engine 128 may be further configured to generate a member activity plan for coaching the member based at least in part on the determined member responses. In this regard, a member activity plan generated by the clinical rules engine may comprise content (e.g., information, further assessment tools, and/or the like) for addressing problems determined by the clinical rules engine 128 based on the member responses. For example, if a member indicates in a response to an assessment question that he is a smoker, the clinical rules engine 128 may be configured to include content counseling the member on quitting smoking in the member activity plan. In another example, if member responses to assessment questions indicate the member is not taking appropriate measures for treatment of a medical condition, the clinical rules engine 128 may be configured to include content in the member activity plan for coaching the member how to take appropriate measures for treatment of the medical condition.

In some embodiments, the clinical rules engine 128 is configured to generate the member activity plan in real time as member responses to one or more assessment questions are determined. Such real time generation of the member activity plan may enable the nurse coach to coach the member to address one or more problems prior to completion of every assessment question in the blended co-morbid assessment question set. In such embodiments, the clinical rules engine 128 may, for example, be configured to generate and/or update the generated member activity plan after each response is determined and/or after responses to a logical grouping of assessment questions (e.g., all assessment questions about a single topic) is determined.

The clinical rules engine 128 may be configured to cause a graphical user interface to be displayed such that the member activity plan is accessible to the nurse coach to enable the nurse coach to coach the member based on the content in the member activity plan. In embodiments wherein the member activity plan is generated in real time, the nurse coach may access the member activity plan at any time during a conversation with the member to address problems. For example, the nurse coach may access content of the member activity plan to coach the member on critical issues rather than first completing the entire set of blended co-morbid questions. In another example, the nurse coach may access content of the member activity plan to coach the member prior to completion of the entire set of blended co-morbid questions to keep the member engaged and to give something back to the member earlier in a conversation. This giving back may build trust, offer immediate value, and improve likelihood of future successful contacts with the member, and thus may improve the results of a care management program utilizing embodiments of the invention.

In some embodiments, the clinical rules engine 128 is configured to determine a priority for one or more problems determined based on the member responses to assessment questions. The clinical rules engine 128 may be configured to determine the priority, through a predefined ordering. Additionally or alternatively, the clinical rules engine 128 may be configured to determine the priority from drivers (e.g., scores) for the respective conditions with which the problems are associated. In some embodiments, problems determined based on responses to barriers and common care assessment questions may be allocated the highest priority such that the problems may be addressed first. Accordingly, the clinical rules engine 128 may be configured to generate a member activity plan comprising content ordered based at least in part upon the determined priorities. In this regard, content for addressing the highest priority problem may, for example, be itemized first on the member activity plan. For example, barriers and common care items may be prioritized at the top of the member activity plan and represent items like lack of medical home, access to food, shelter, support network, tobacco cessation, etc. which should be addressed before a member can make significant behavioral changes to get their medical conditions under management and properly navigate the healthcare system. As an example, ensuring that a member has access to food should be addressed before coaching and counseling on the value of a low sodium diet.

During coaching contacts with a member, the nurse coach may uncover a new problem. In some embodiments of the invention, the clinical rules engine 128 is configured to provide an interface allowing the nurse coach to enter a new problem and the clinical rules engine 128 may then add the new problem to the member activity plan. This Just-in-time (JIT) addition of problems may allow the nurse coach to identify new or re-address critical issues immediately without waiting for another member assessment.

In addition to adding problems on the fly, the nurse coach may also trigger activation by the clinical rules engine 128 (e.g., through user input) of a new member assessment module for a new medical condition and/or non-condition-specific member assessment modules as new issues arise and require intervention and coaching. These modules may allow the nurse coach to trigger modification of the member activity plan by the clinical rules engine 128 to meet the member's most pressing needs without waiting for supporting claims information or another full member assessment.

Figure 3:
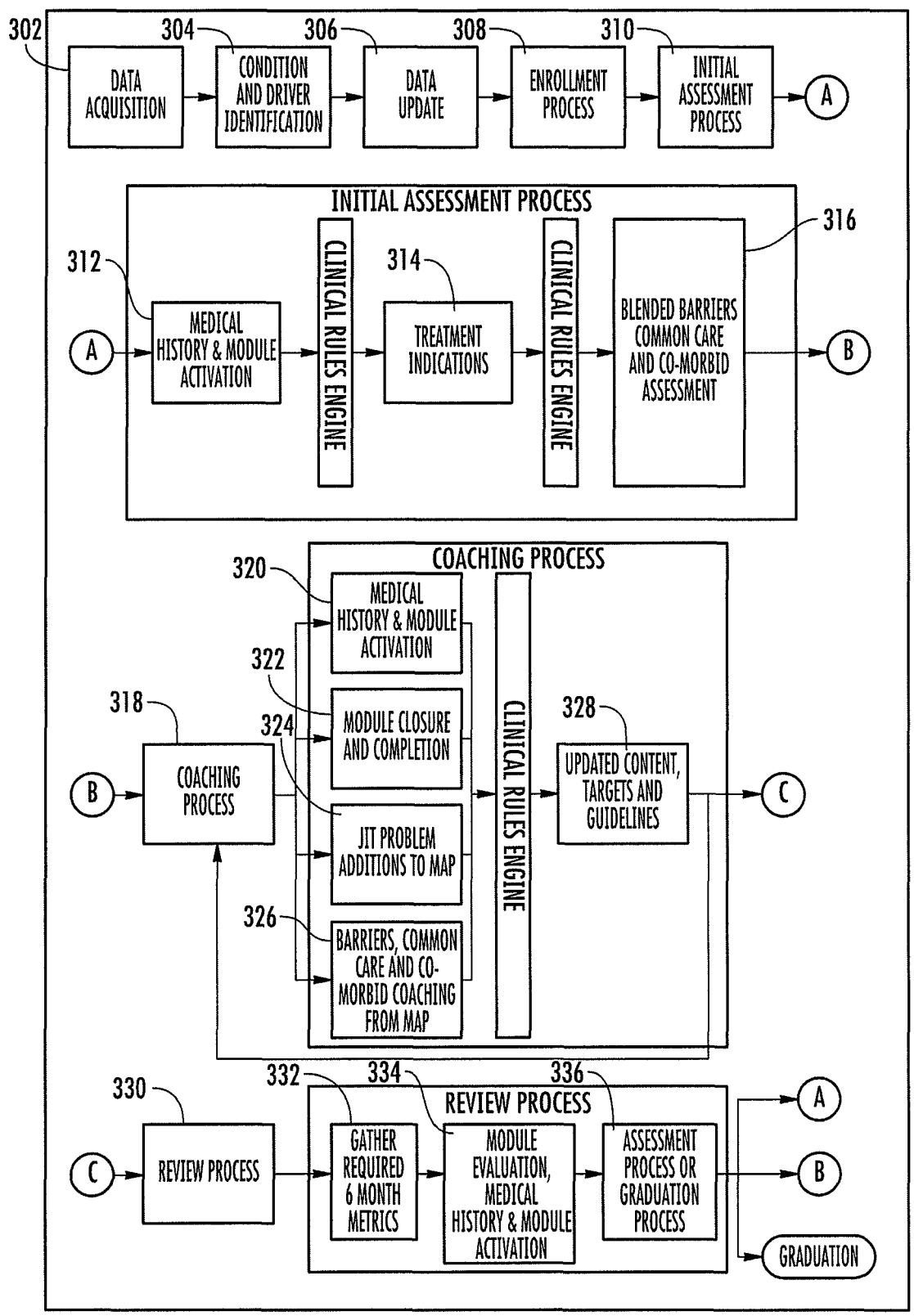
FIG. 3 illustrates a process for facilitating co-morbid care management according to an exemplary embodiment of the present invention.
Figure 26:
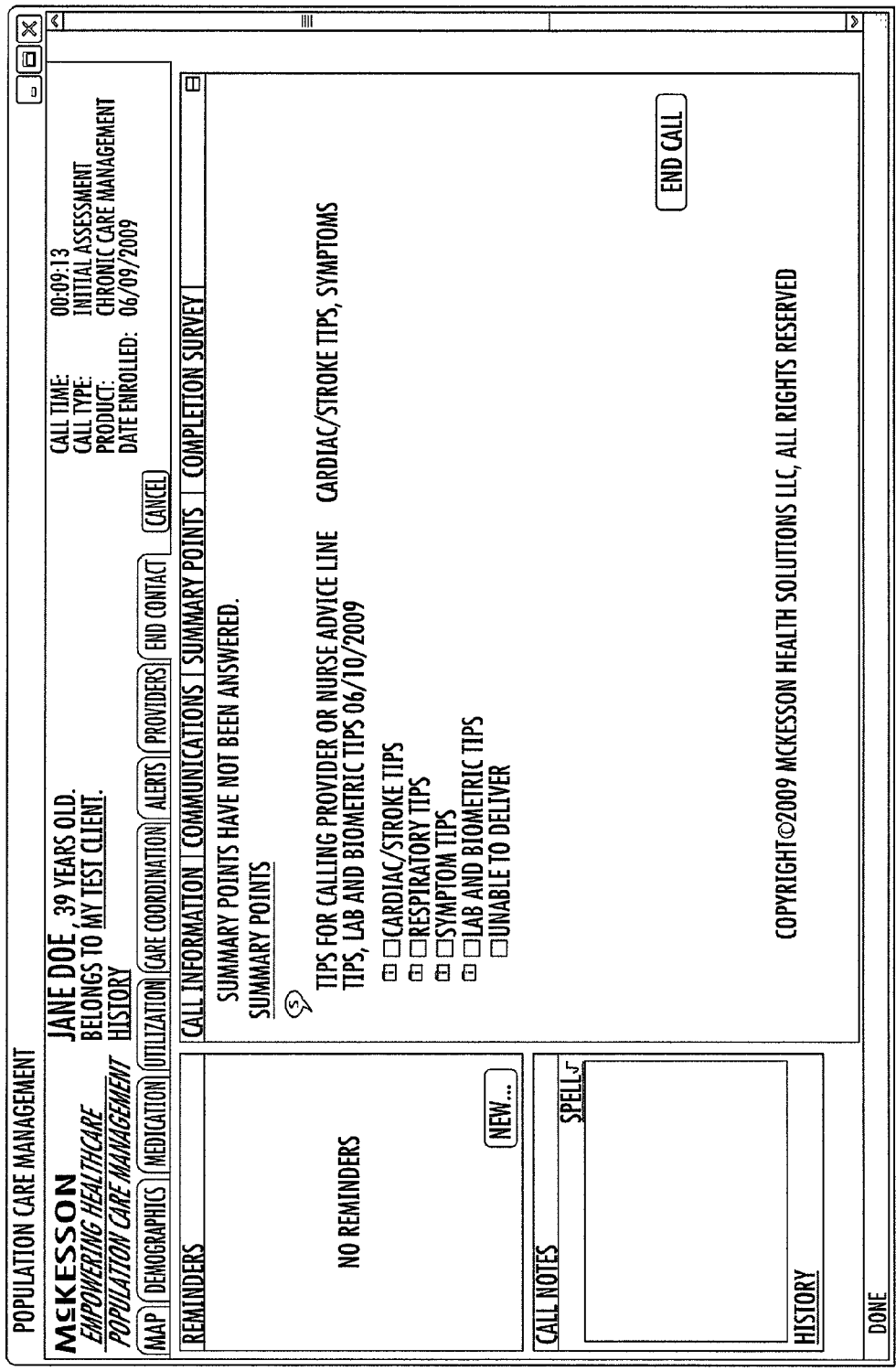

FIG. 3 illustrates a process for facilitating co-morbid care management according to an exemplary embodiment of the present invention. At operation 302, the clinical rules engine 128 may acquire data for determining medical conditions affecting a prospective member of a care management plan. The clinical rules engine 128 may then utilize the acquired data to identify medical conditions affecting the prospective member and calculate a driver score for respective determined conditions, at operation 304. Operation 306 may comprise the clinical rules engine selecting newly acquired members in batches for enrollment contacts by the nurse coaches The prospective member may then be enrolled in the care management program, at operation 308. It will be appreciated, however, that the ordering of the operations to this point is merely for purposes of example and the member may have been enrolled prior to execution of operation 302 (e.g., through a real time referral from another program such as a nurse advice line or direct health plan, provider, case manager or care giver request, and/or the like). Accordingly, operation 302 may comprise acquiring data for an enrolled member rather than a prospective member.

Next, an initial assessment process 310 may be executed. In this regard, the clinical rules engine 128 may determine the medical conditions identified in operation 304 and activate one or more member assessment modules based thereon, at operation 312. Operation 312 may be carried on totally autonomously by the clinical rules engine 128 and/or with input from a nurse coach. In this regard, the nurse coach may select a subset of the determined medical conditions to activate member assessment modules for and/or may select additional member assessment modules for activation, such as based on a conversation with the member about the member's goals and/or additional medical conditions affecting the member. The clinical rules engine 128 may then derive treatment indications (e.g., from the member's medical history) for use in generating a blended co-morbid assessment question set for the member, at operation 314. Operation 316 may then comprise the clinical rules engine generating the blended co-morbid assessment question set, which may then be used by the nurse coach to assess the patient.

Upon completion of one or more assessment questions of the blended co-morbid assessment question set, the clinical rules engine 128 may be configured to generate a member activity plan based on determined member responses to the assessment questions. The member activity plan may be used by the nurse coach in a coaching process 318. The coaching process may be flexible to allow for a conversational dialogue. In this regard, while using the member activity plan for a coaching process, the nurse coach may carry out a number of activities. The nurse coach may select a problem identified on the member activity plan and use content provided for addressing the problem for coaching the member, at operation 326. Additionally or alternatively, the nurse coach may select a new member assessment module for activation by the clinical rules engine 128 without revisiting the initial assessment process, at operation 320. The nurse coach may also make a just in time addition of a problem to the member activity plan, at operation 324, such as to add a problem in addition to those determined by the clinical rules engine 128 based on determined responses to assessment questions.

The nurse coach may additionally return to the assessment process at any time to complete assessment questions from the blended co-morbid assessment question set that have not already been completed. In this regard, embodiments of the invention allow the nurse coach to mix coaching in with the assessment process to provide a more flexible dialog with the member. Once responses to all assessment questions associated with a particular module (e.g., the medical condition associated with the module) have been determined and problems determined based thereon have been addressed through coaching from the member activity plan, the nurse coach can verify that the problems have been addressed through coaching by providing an indication via the user interface 126. The clinical rules engine 128 may in turn close the module upon determining completion, at operation 322.

The clinical rules engine 128 may update content of the member activity plan, targets, guidelines, and/or goals at any point during the coaching process, at operation 328. However, in some embodiments, the clinical rules engine 128 may carry out operation 328 upon completion of a conversation between the nurse coach and the member.

At the onset of a subsequent conversation between the nurse coach and the member, the nurse coach may carry out a review process 330. The review process 330 may comprise gathering metrics that have occurred since the previous conversation (e.g., in the last 6 months), at operation 332. The review process may further comprise the clinical rules engine 128 performing a further evaluation of medical history data and the gathered metrics to determine whether any new medical conditions are affecting the member and, if so, activating appropriate member assessment modules, at operation 334. Operation 336 may comprise the nurse coach administering a further assessment process (e.g., continuing with assessment questions of the co-morbid assessment question set for which responses have not previously been determined and/or determining responses to assessment questions newly added in operation 334). The nurse coach may then return to the initial assessment process 310 and/or coaching process 318 as needed for the member.

FIGS. 4-28 illustrate screenshots of a graphical user interface for facilitating co-morbid care management according to an exemplary embodiment of the invention. It will be appreciated that the contents of these screenshots are provided merely for purposes of example and not by way of limitation. Accordingly, other selections and arrangements of interface elements are contemplated within the scope of the invention. Further, the actual contents of the screenshots may depend on a particular member's medical conditions and responses to assessment questions. Accordingly, the screenshot contents merely illustrate content for an example member, Jane Doe.

Figure 4:
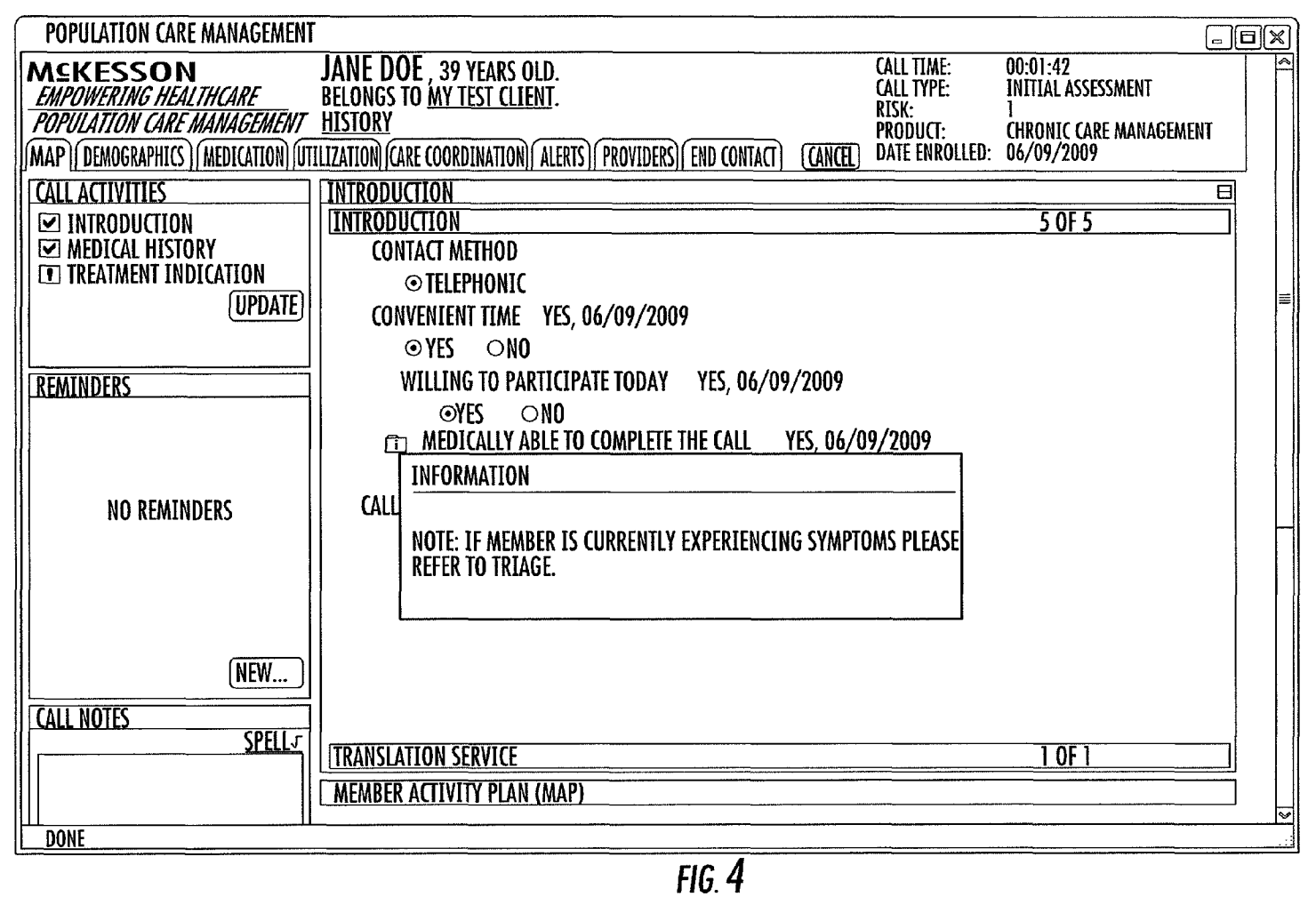
Figure 5:
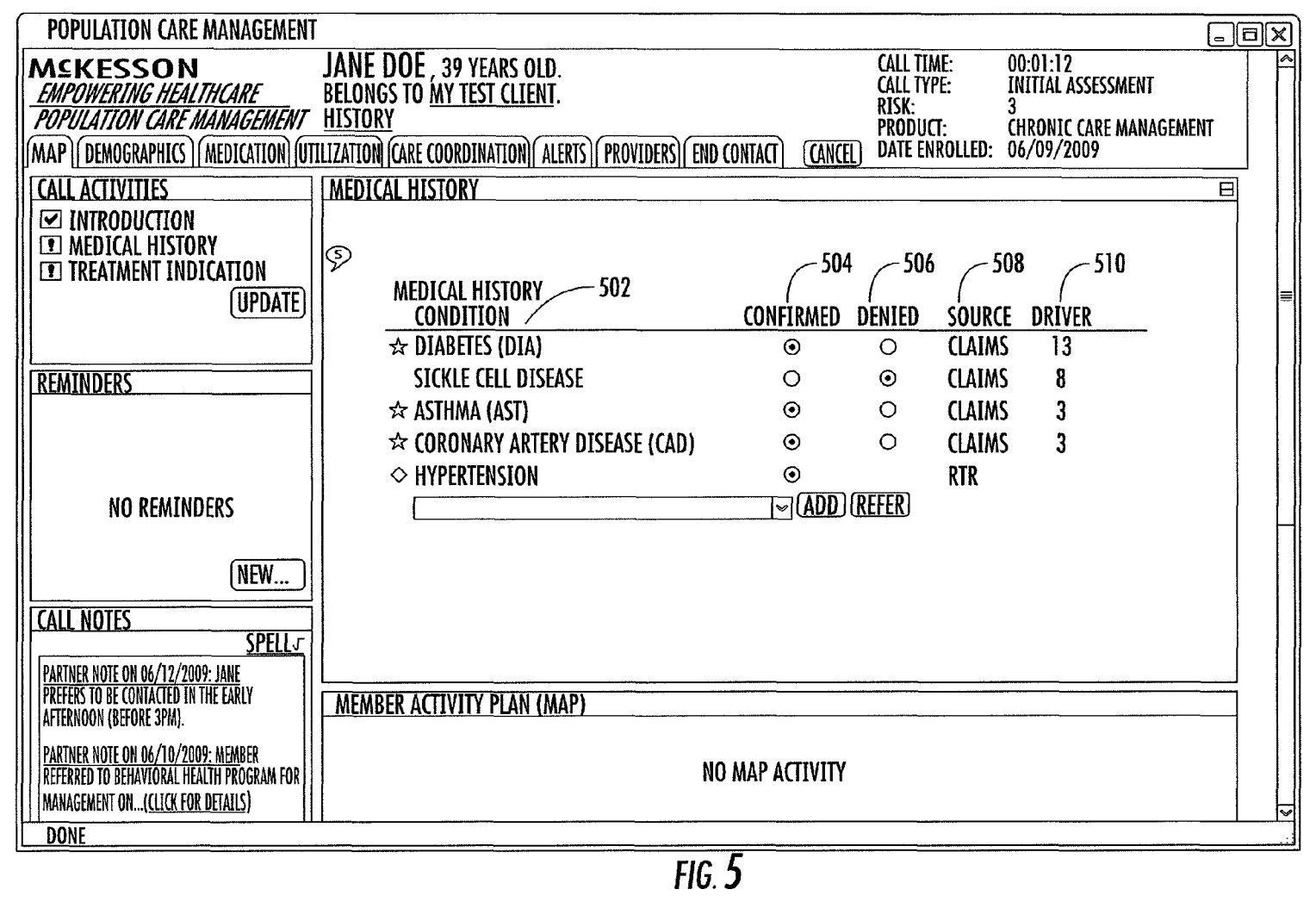

This graphical user interface may be controlled and caused to be displayed by the clinical rules engine 128. In this regard, the clinical rules engine 128 may be configured to determine user interactions (e.g., inputs by a nurse coach) with the graphical user interface and perform various functionalities based on the user interactions. FIG. 4 illustrates a screen that may be displayed to a nurse coach at the outset of a conversation with a member by which the nurse coach may introduce the purpose of the conversation and determine the member's willingness to participate. The conversation may occur via a phone conversation, text messaging conversation, instant messaging conversation, conversation via video conferencing, conversation via other electronic means, face-to-face conversation, and or the like. FIG. 5 illustrates a listing of medical conditions 502 determined to be affecting the member by the clinical rules engine 128. The nurse coach may converse with the member to determine whether the member confirms 504 or denies 506 the existence of the medical conditions and whether the member wishes to receive coaching with respect to any of the medical conditions. The medical conditions may also include an indication of a source 508 based upon which the clinical rules engine 128 determined existence of the medical condition. The source may comprise any data accessible to the clinical rules engine 128 (e.g., claims, a real time referral (RTR), member response data entered by the nurse coach, payer, provider, member medical history, electronic medical records, and/or the like). The medical conditions may further include an indication of a respective driver score 510.

Figure 6:
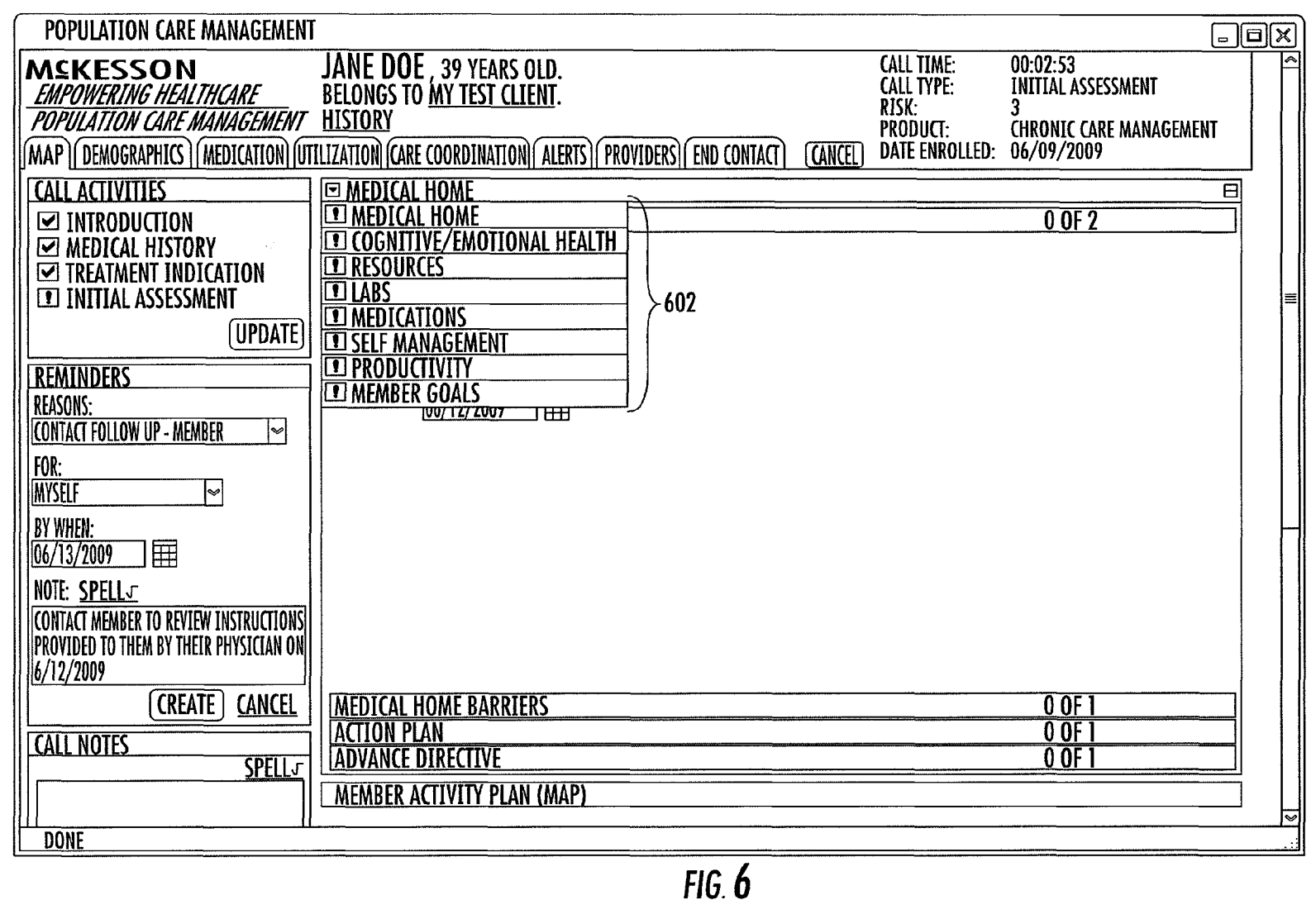
Figure 7:
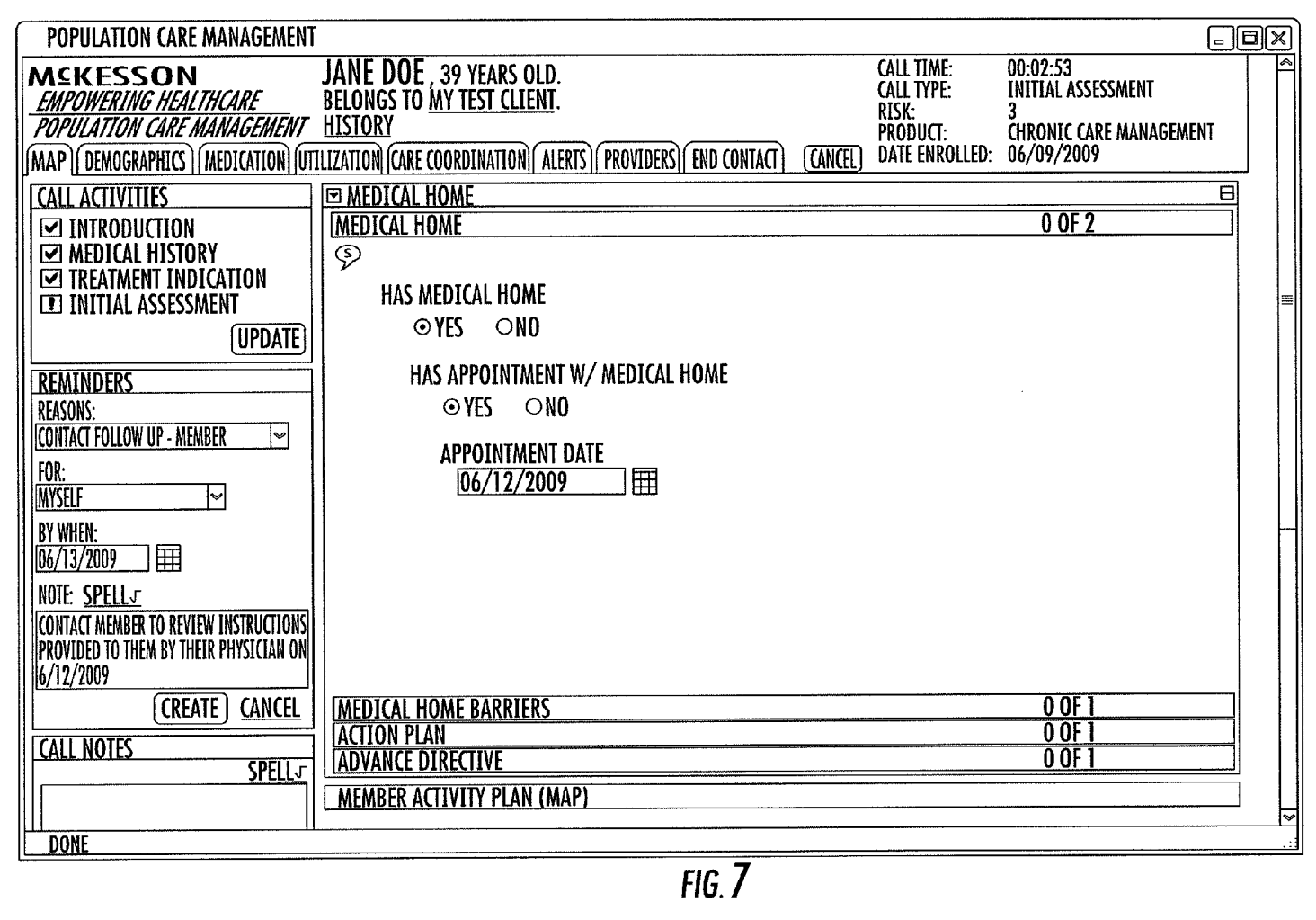
Figure 8:
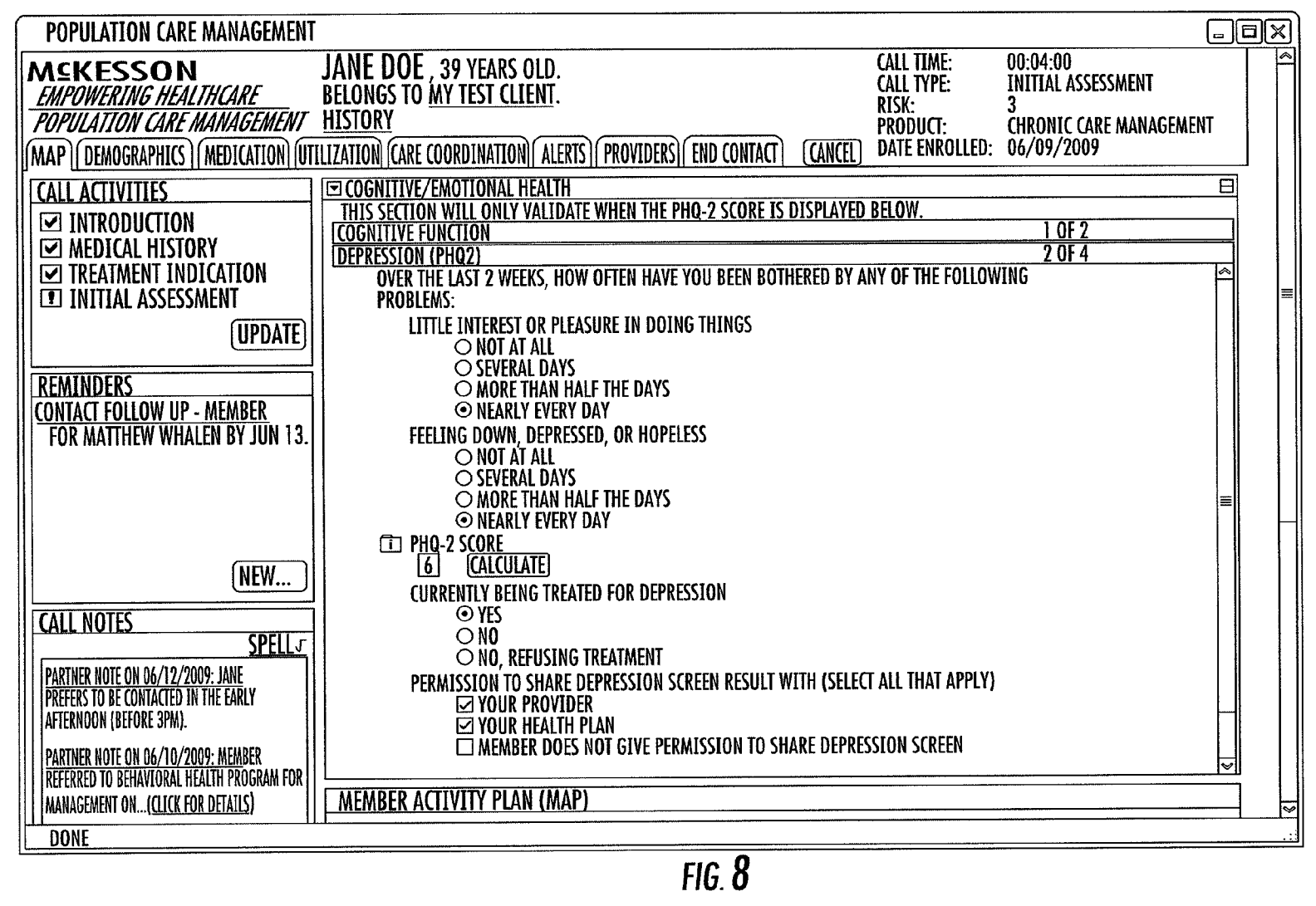
Figure 9:
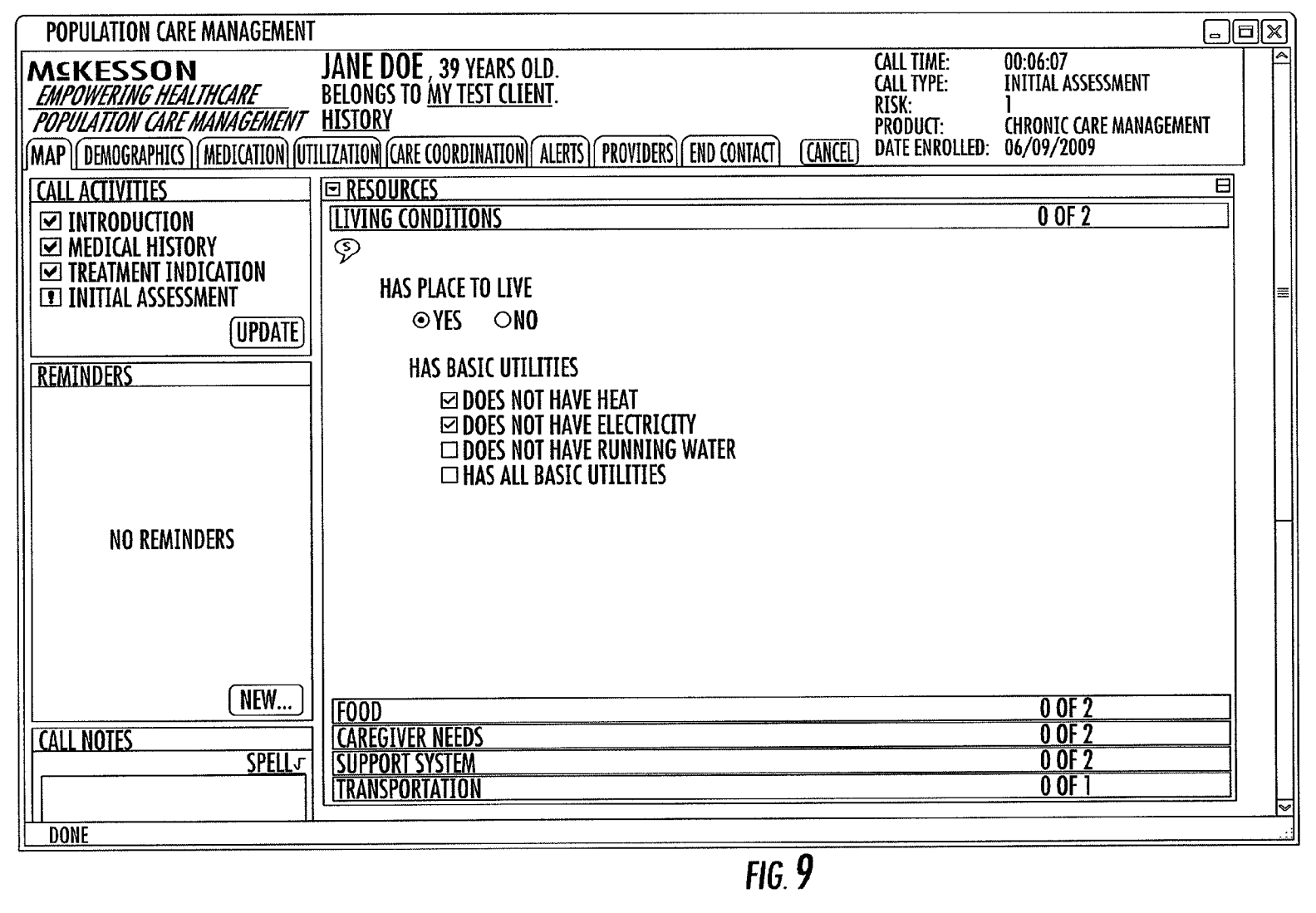
Figure 12:
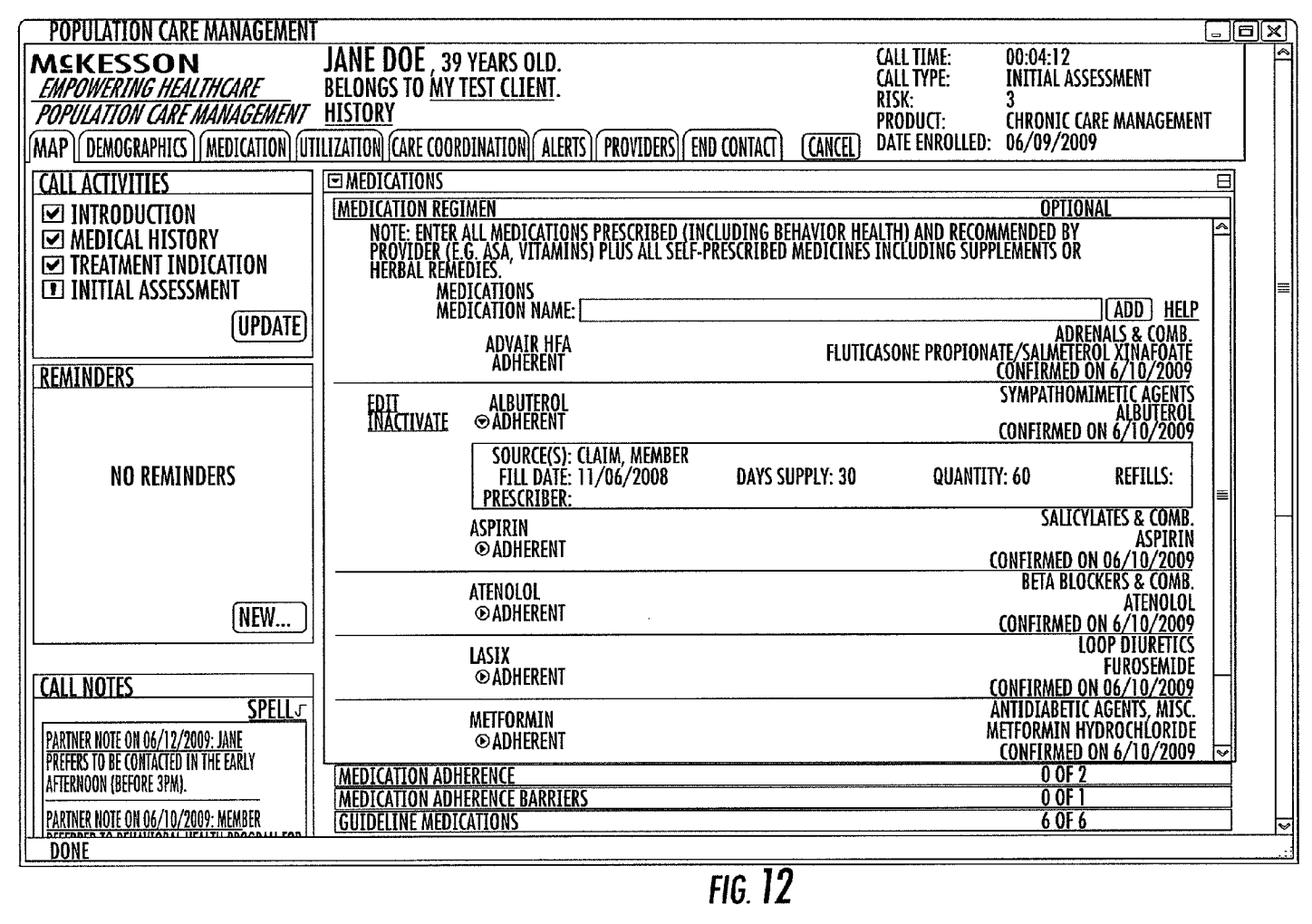

FIG. 6 illustrates a screen that may be accessible to a nurse coach following generation of the blended co-morbid assessment question set. The screen may include a menu 602 allowing the nurse coach to select from groupings of assessment questions (e.g., medical home, cognitive/emotional health, resources, labs, medications, self management, productivity, member goals, and/or the like). The clinical rules engine 128 may be configured to determine a selection of a grouping of assessment questions and, in response to the determination, cause the assessment questions from the selected grouping to be displayed to enable the nurse coach to assess the member and document member responses. FIG. 7 illustrates a screen with assessment questions with respect to the member's medical home. FIG. 8 illustrates a screen having assessment questions including a screening tool that may be used to score a member with respect to the member's cognitive/emotional health. The screening tool may comprise any clinically appropriate and/or standard tool for screening an individual with respect to a condition, such as, for example, a PHQ-2 depression screening test. FIG. 9 illustrates a screen having assessment questions with respect to the member's resources (e.g., living conditions, food, caregiver needs, support system, transportation, and/or the like). FIG. 10 illustrates a screen having assessment questions with respect to the member's most recent lab measures (e.g., weight, cholesterol, blood pressure, and/or the like). FIG. 11 illustrates a screen having assessment questions with respect to the member's medication regimen and how that medication regimen relates to the evidence based guideline medications recommended for that member based on their medical conditions and treatment indications. In this regard, FIG. 11 illustrates assessment questions with respect to guideline medications that a member should be taking based on the medical conditions determined to be affecting the member by the clinical rules engine 128. The nurse coach may then assess whether the member is taking the suggested guideline medications. FIG. 12 illustrates a screen having assessment questions with respect to actual medications that the clinical rules engine 128 has determined that the patient is taking or has taken (e.g., from claims information, medical history, member responses, provider reported, and/or the like).

FIG. 13 illustrates a screen having assessment questions with respect to the member's self management of medical conditions determined to be affecting the patient. As illustrated, these questions comprise a blended listing of assessment questions for the patient's determined medical conditions based upon the blended co-morbid assessment question set generated by the clinical rules engine 128 from the activated member assessment modules. In this regard, the group of assessment questions 1302 are directed to self management of diabetes, the group of assessment questions 1304 are directed to self management of coronary artery disease, and the assessment question 1306 may be directed to self management of a barrier and common care driver of member health (e.g., avoiding secondhand smoke).

Figure 14:
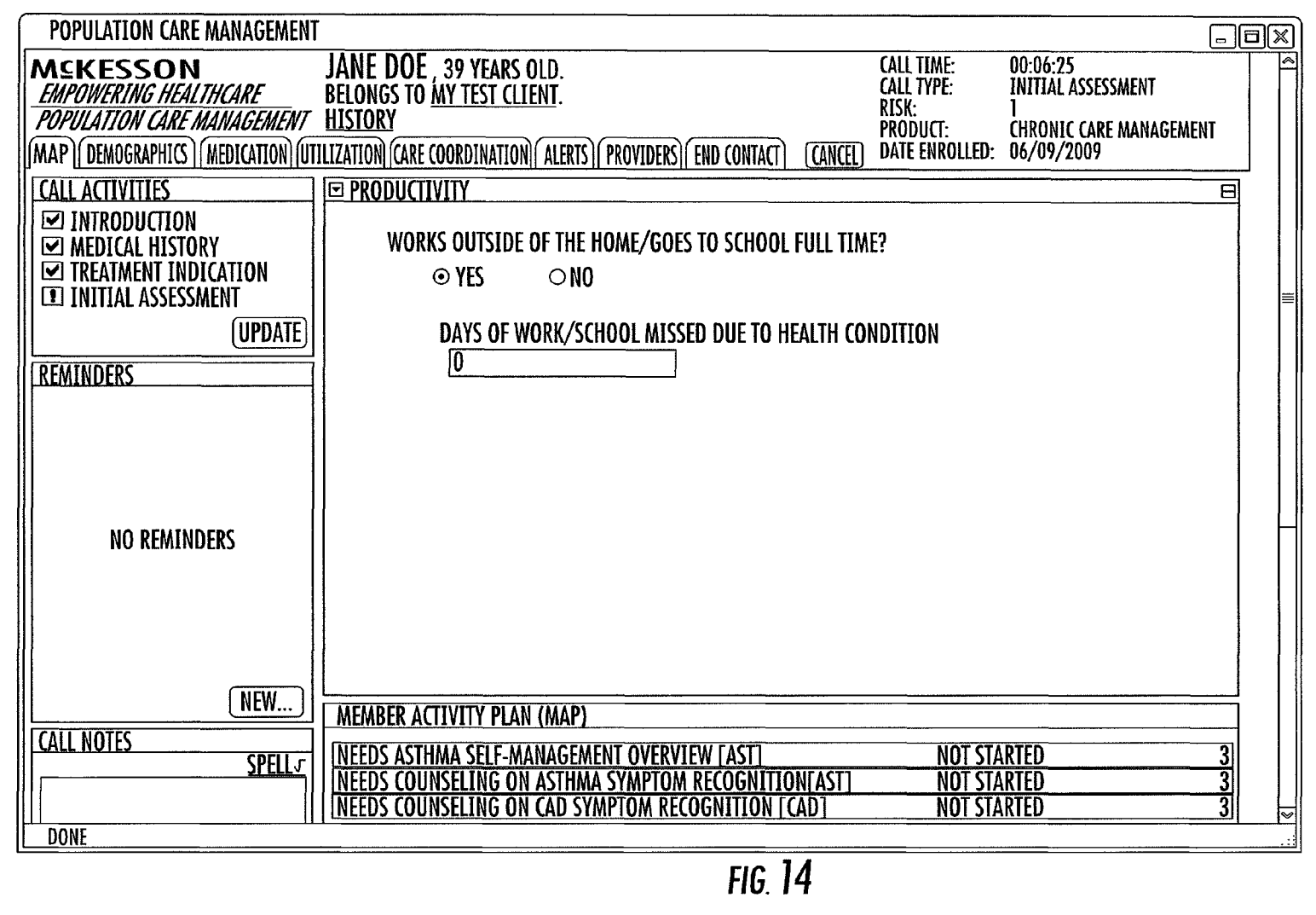
Figure 15:
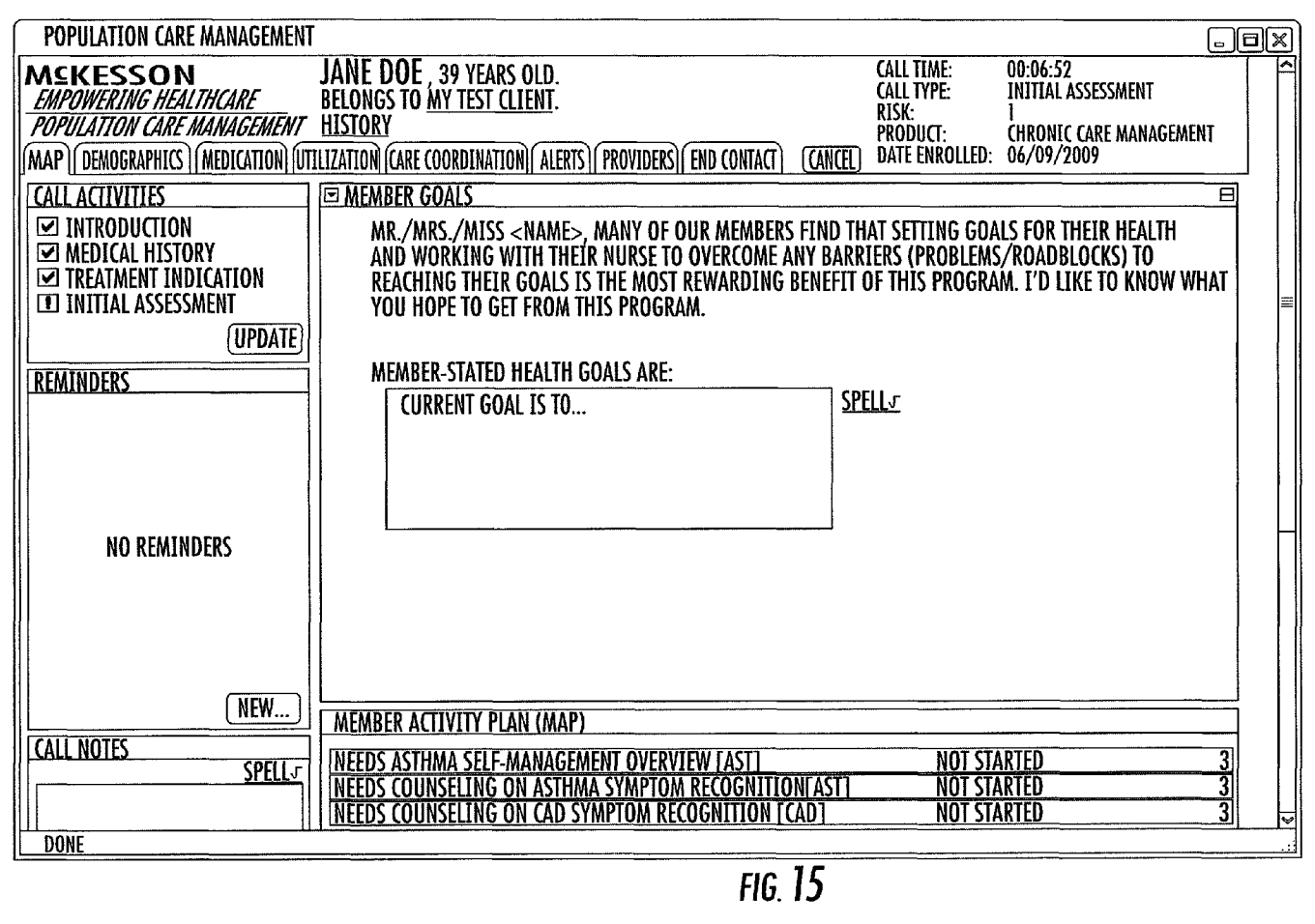
Figure 16:
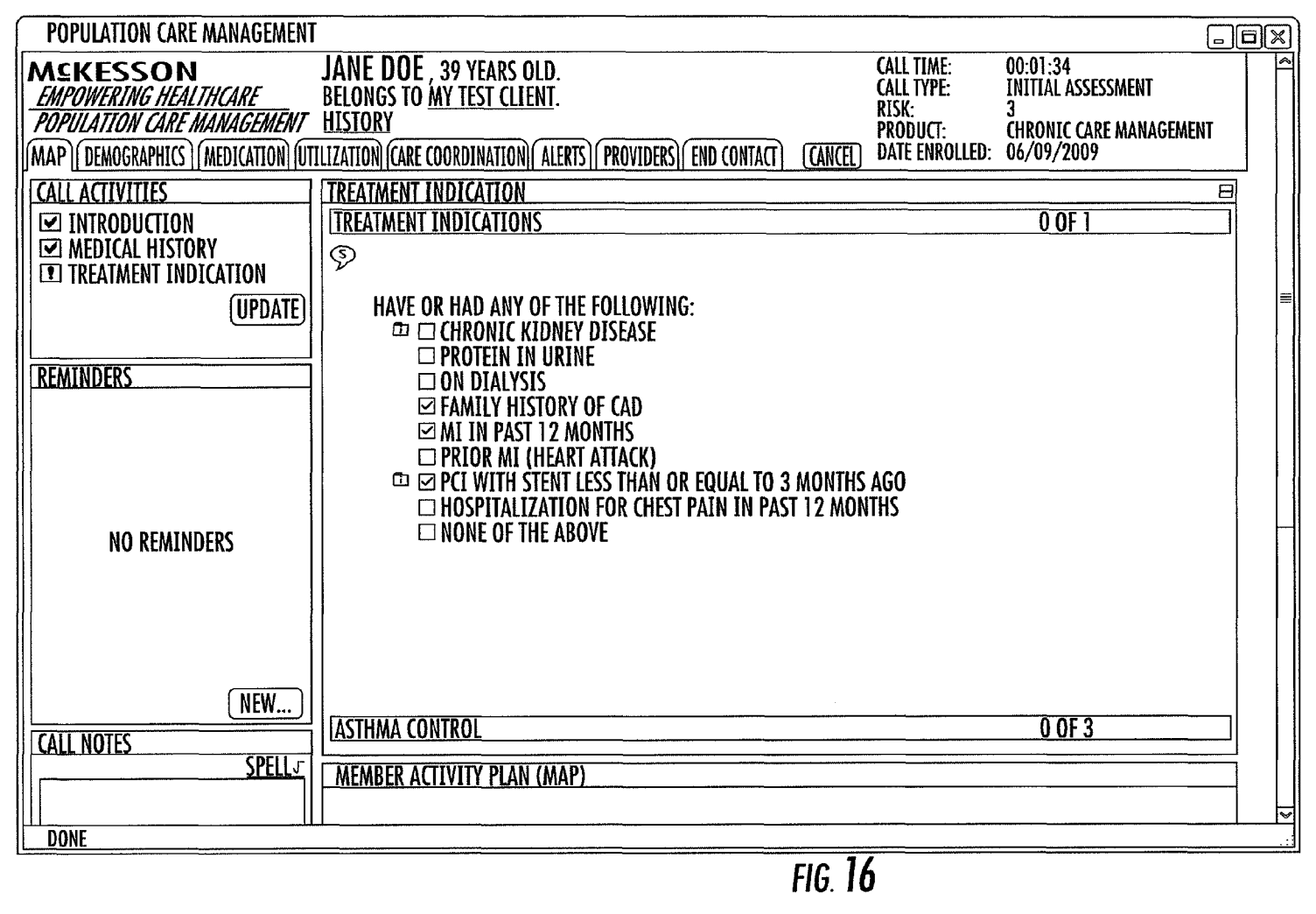

FIG. 14 illustrates a screen having assessment questions with respect to the member's productivity. FIG. 15 illustrates a screen having an assessment question with respect to the member's goals he wishes to achieve from participation in the care management plan. FIG. 16 illustrates a screen having assessment questions with respect to member treatment indications that may be used by the clinical rules engine 128 for generation of the blended co-morbid assessment and/or member activity plan. FIG. 17 illustrates an alerts assessment screen. The alerts assessments may be generated by the clinical rules engine 128 in response to member responses to assessment questions, updates to labs/tests/biometrics, updates to medications, and or the like, such as in accordance with predefined rules the clinical rules engine 128 is configured to implement. Additionally or alternatively, they may be selected by the nurse coach. The clinical rules engine 128 may be configured to communicate alerts and/or responses to alert assessments to a third party (e.g., a provider, payer, physician, and/or the like), via electronic communication means (e.g., email, fax, automated voice call, and/or the like).

Figure 18:
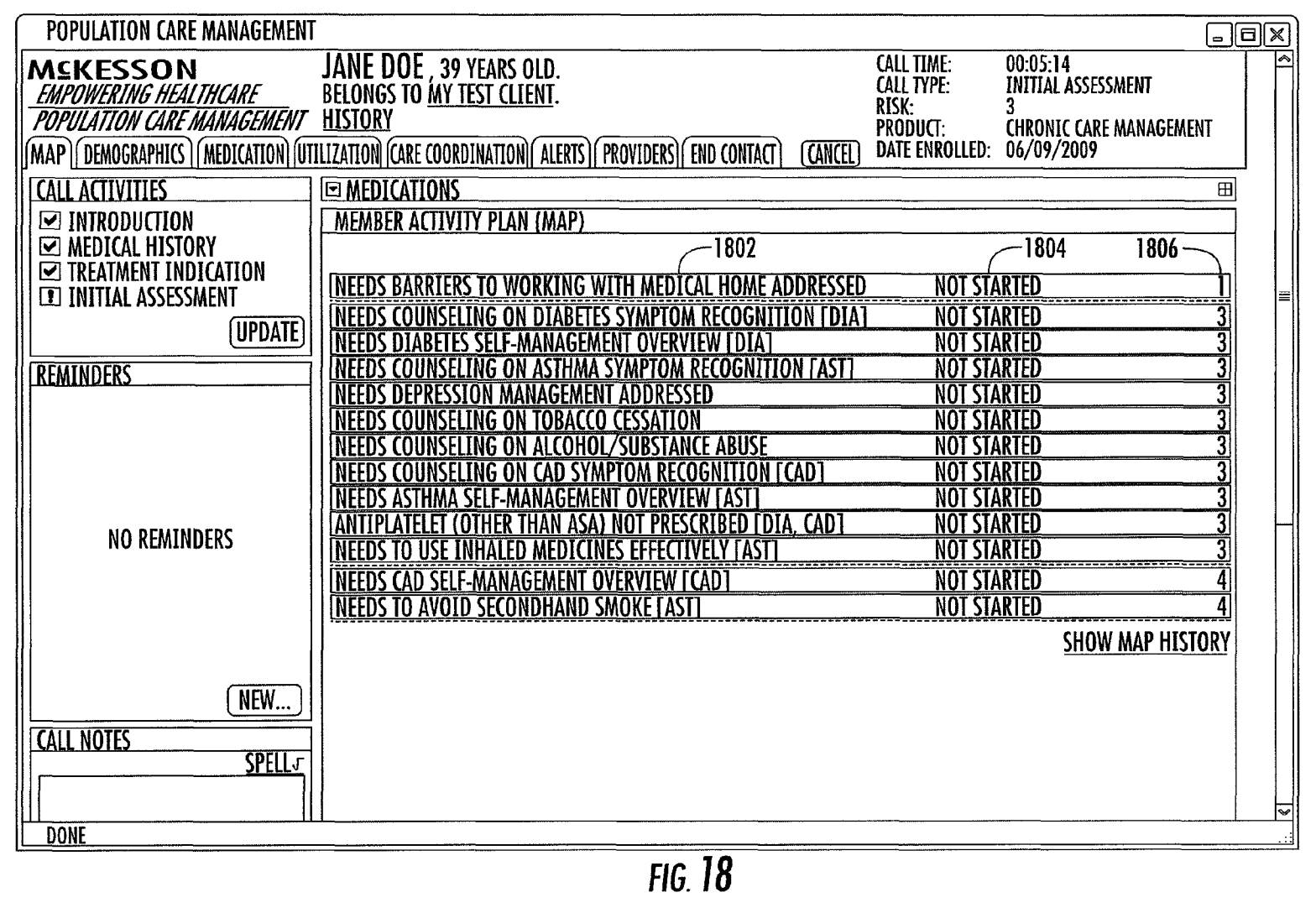

FIG. 18 illustrates a problem topic index to a member activity plan that may be generated by the clinical rules engine 128 based upon determined member responses to assessment questions. Each topic may include a description 1802 of the topic, a status indication 1804 (e.g., not started, in progress, completed, or the like), and a priority ranking 1806. The topics may be ordered in the index based upon the priority ranking. In FIG. 18, the topic "Needs barriers to working with medical home addressed" is prioritized first, as this is considered to be a barrier to care issue that may need to be resolved prior to coaching on other problems.

Figure 19:
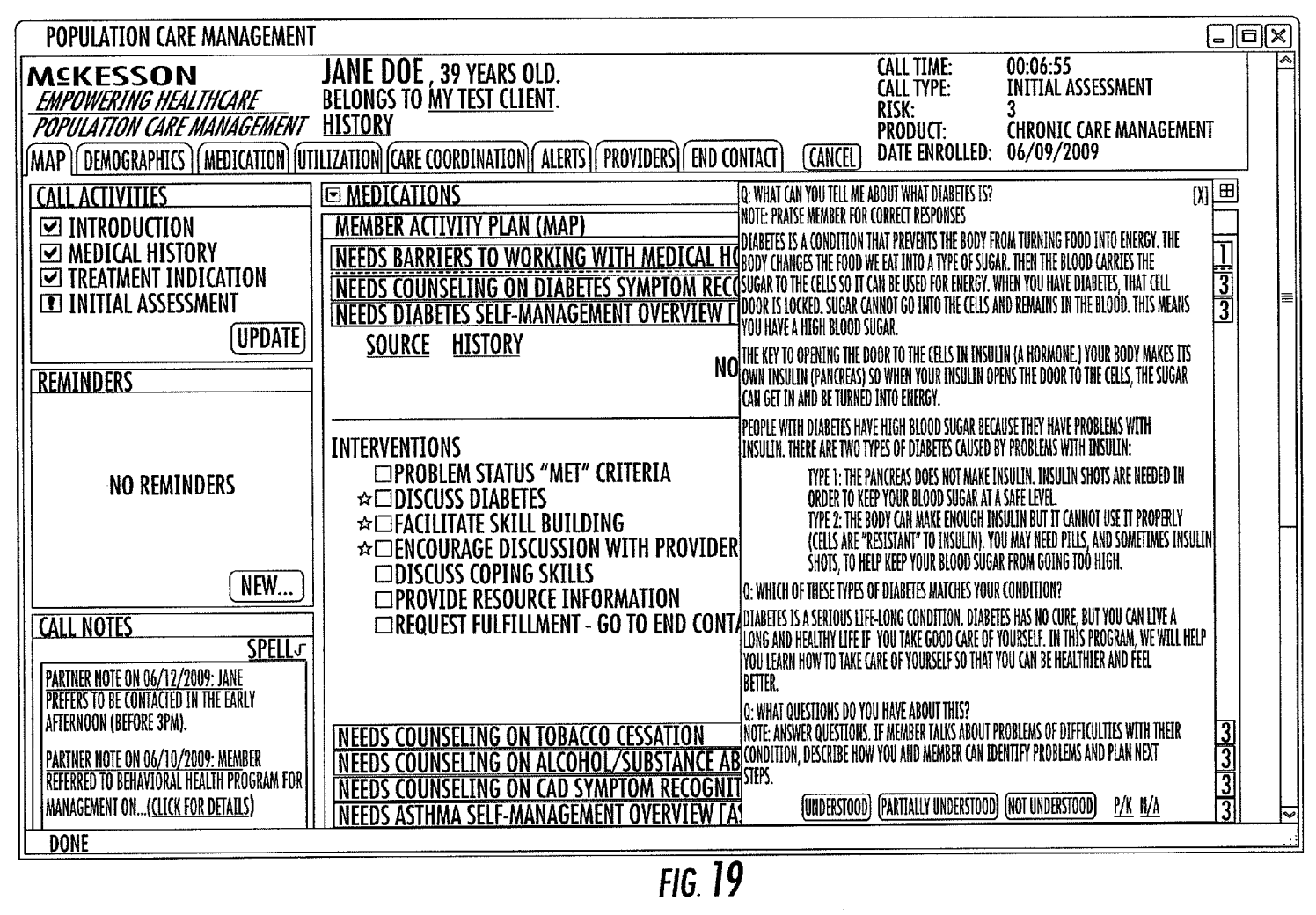
Figure 20:
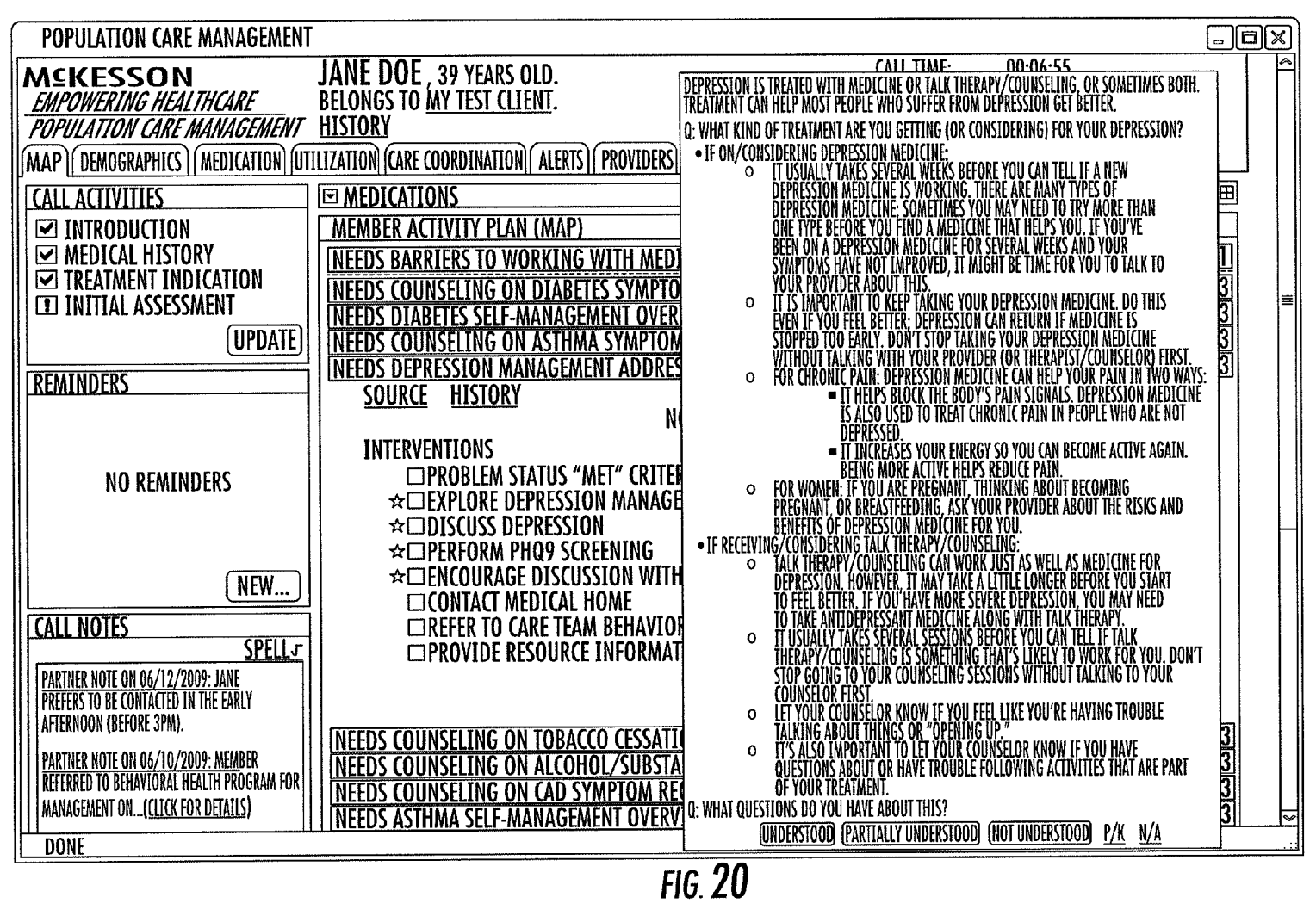
Figure 21:
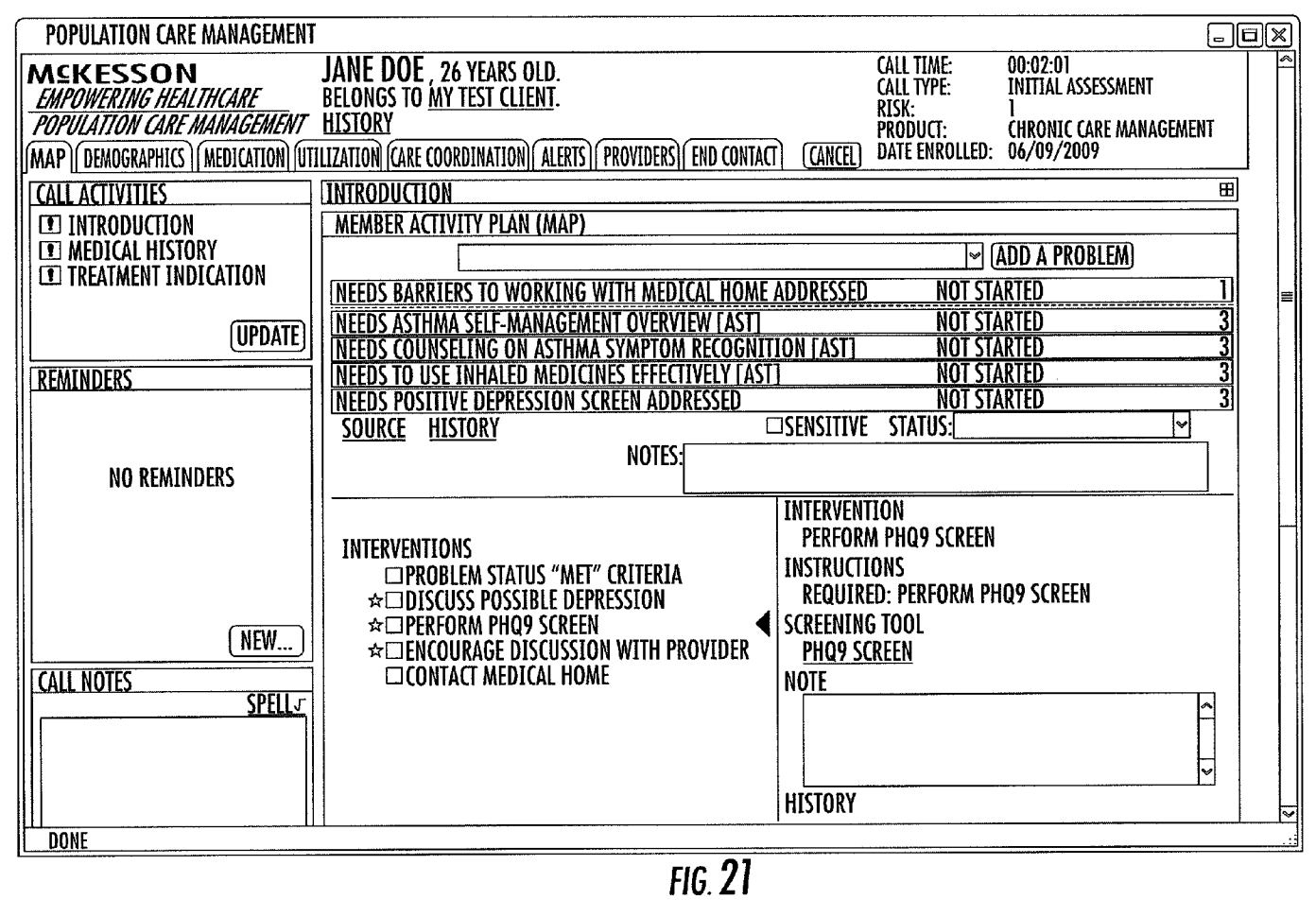

FIG. 19 illustrates coaching content that may be provided for addressing determined problems with respect to the member's self-management of diabetes. FIG. 20 illustrates coaching content that may be provided for addressing a member's management of depression. FIG. 21 illustrates interventions and further screening tool content for addressing a positive depression screen as determined by the clinical rules engine 128 based upon member responses to assessment questions. FIG. 22 illustrates a further depression assessment screening tool that may be accessible from the content of FIG. 21. In this regard, content provided by the member activity plan may include additional screening tools and assessments to further assess the member based upon determined responses to assessment questions from the blended co-morbid assessment question set.

Figure 23:
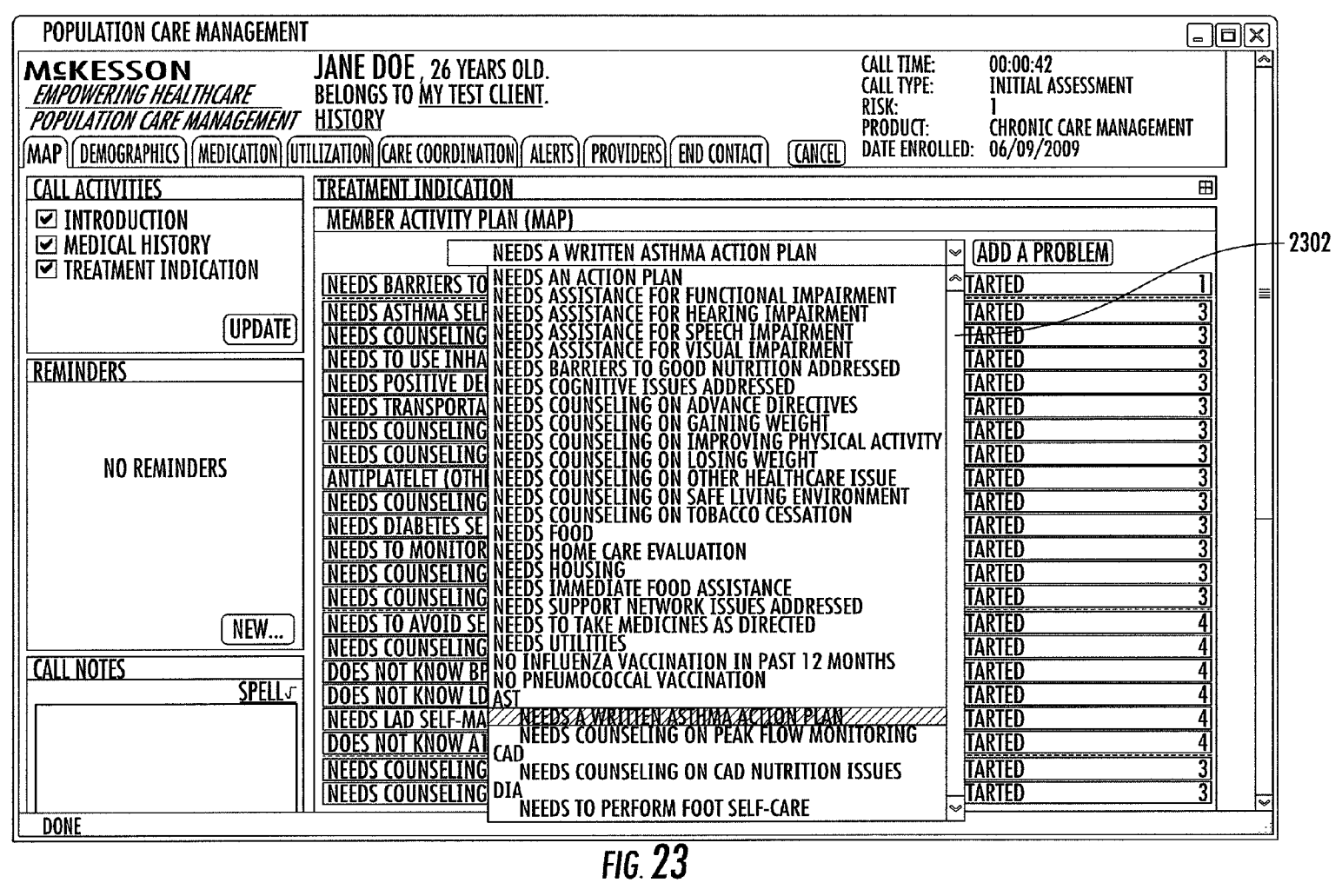

FIG. 23 illustrates an interface according to one embodiment of the invention by which a nurse coach may add a just in time problem to the member activity plan. In this regard, FIG. 23 illustrates a drop down menu 2302 by which a nurse coach may select a problem from a list of predefined problems. The clinical rules engine 128 may then determine selection of a problem for addition to the member activity plan and update the member activity plan to include content for addressing the selected problem.

FIGS. 24-27 illustrate screenshots of documentation questions and options that may be provided upon conclusion of a conversation between the nurse coach and the member. In this regard, the nurse coach may document the results and topics covered by the conversation, schedule a next conversation, and/or the like. The documentation questions and options may further provide options to schedule information packets and/or links thereto to be sent to the member (e.g., via mail, electronic communication, and/or the like).

Figure 28:
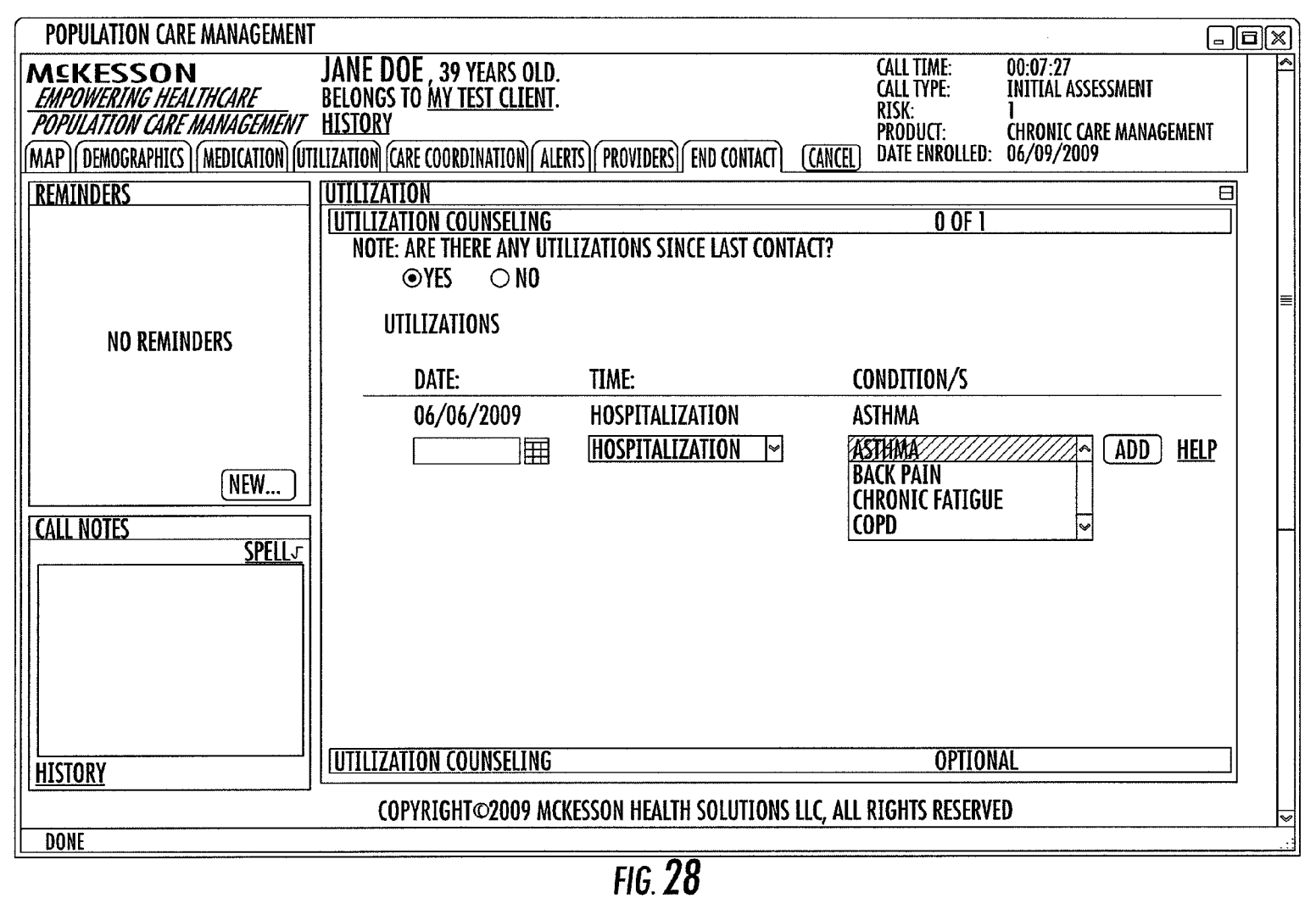

FIG. 28 illustrates a screen with assessment questions with respect to utilization that a nurse coach may access during a subsequent conversation with the member. In this regard, the nurse coach may document any treatment the member has received since the last conversation, a new problem or condition faced by the member since the last conversation, and/or the like.

Figure 29:
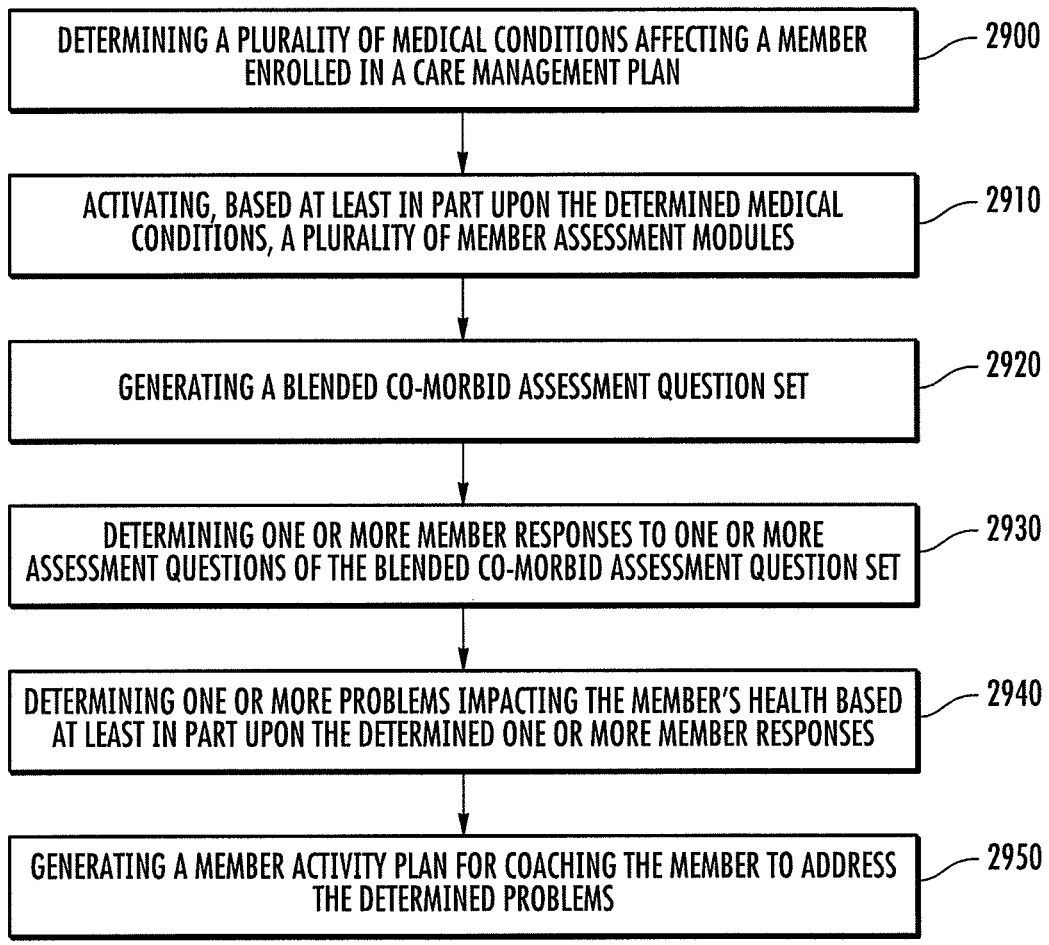
FIG. 29 illustrates a flowchart according to an exemplary method for facilitating co-morbid care management according to an exemplary embodiment of the invention.

FIG. 29 illustrates a flowchart according to an exemplary method for facilitating co-morbid care management according to an exemplary embodiment of the invention. Operations illustrated in FIG. 29 may, for example, be performed by and/or with the assistance of the clinical rules engine 128. The method may include determining a plurality of medical conditions affecting a member enrolled in a care management plan, at operation 2900. Operation 2910 may comprise activating, based at least in part upon the determined medical conditions, a plurality of member assessment modules. The method may further include generating a blended co-morbid assessment question set, at operation 2920. Operation 2930 may comprise determining one or more member response to one or more assessment questions of the blended co-morbid assessment question set. The method may additionally include determining one or more problems impacting the member's health based at least in part upon the determined one or more member responses, at operation 2940. Operation 2950 may comprise generating a member activity plan for coaching the member to address the determined problems.

FIG. 29 is a flowchart of a system, method, and computer program product according to exemplary embodiments of the invention. It will be understood that each block or step of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices of a server, desktop computer, laptop computer, mobile computer, or other computing device (e.g., the care management apparatus 102, user terminal 208, combination thereof, and/or the like) and executed by a processor (e.g., the processor 120) in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s) or step(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s) or step(s). The computer program instructions of one or more computer program products may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the flowchart block(s) or step(s).

Accordingly, blocks or steps of the flowchart support combinations of means for performing the specified functions and combinations of steps for performing the specified functions. It will also be understood that one or more blocks or steps of the flowchart, and combinations of blocks or steps in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processor may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

As such, then, some embodiments of the invention provide several advantages to payers and members of care management plans. Embodiments of the invention provide for a care management program that is member-centric in that assessment and coaching is customized based on multiple medical conditions affecting a member enrolled in a care management plan. According to some embodiments of the invention, a plurality of medical conditions affecting a member are determined and then a blended co-morbid assessment question set is generated based on the determined plurality of medical conditions such that a single assessment question set is generated that is member-specific and concurrently addresses multiple medical conditions affecting the member. Accordingly, the member may be spared from redundant questioning that may occur if separate condition-specific assessment question sets were used to separately assess the member with respect to each medical condition affecting the member. Some embodiments of the invention wherein a blended co-morbid assessment question set is generated further ensure that only assessment questions that are appropriate given the mix of medical conditions affecting the member are included in the co-morbid assessment question set. Accordingly, if coaching is given to a member based on responses to assessment questions in the blended co-morbid assessment question set, the member may be spared being given conflicting advice or advice targeted to one medical condition affecting the member that may be inappropriate given a second medical condition affecting the member.

Some embodiments of the invention further provide for generation of a member activity plan based at least in part on member responses to assessment questions in the blended co-morbid assessment question set. Such embodiments enable tailored coaching of the member to address factors that may be affecting the member's health in view of the member's existing medical conditions, risk factors, and/or responses to assessment questions. Some embodiments provide for generation of the member activity plan in real time as member responses to assessment questions in the blended co-morbid assessment question set are determined so that a nurse-coach assessing and coaching the member may provide coaching to the member prior to completion of all of the assessment questions in the blended co-morbid assessment question set. Such embodiments may facilitate a more conversational assessment-coaching session so that a member may derive some benefit earlier in the session and remain more engaged during the duration of the assessment-coaching session than the member might if the member had to answer every assessment question prior to receiving any coaching.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method for facilitating co-morbid care management, the method comprising:
    determining a plurality of medical conditions affecting a member enrolled in a care management plan;
    activating, based at least in part upon the determined medical conditions, a plurality of member assessment modules, wherein each activated member assessment module is associated with a respective determined medical condition, and wherein each activated member assessment module comprises a set of assessment questions targeted to the medical condition with which the member assessment module is associated; and
    generating, by a processor, a blended co-morbid assessment question set based at least in part on the assessment question sets of the activated member assessment modules by blending the assessment question sets of the activated member assessment modules into a blended co-morbid assessment question set;
    wherein blending the assessment question sets of the activated member assessment modules into a blended co-morbid assessment question set comprises:
        determining that the assessment question sets of the activated member assessment modules comprise at least one conflicting assessment question by identifying at least one question that is medically appropriate for a first one of the activated member assessment modules and medically inappropriate for a second one of the activated member assessment modules; and
        when the assessment question sets of the activated member assessment modules comprise at least one conflicting assessment question:
            determining a medically appropriate assessment question based on the conflicting assessment question, wherein the medically appropriate assessment question is appropriate for the activated member assessment modules; and
            including the medically appropriate assessment question in the blended co-morbid assessment question set.

2. The method of claim 1, wherein blending the assessment question sets of the activated member assessment modules into a blended co-morbid assessment question set comprises eliminating a duplicate assessment question when an assessment question is included in more than one of the assessment question sets of the activated member assessment modules so that the blended co-morbid assessment question set comprises a set of unique assessment questions.

3. The method of claim 1, wherein generating the blended co-morbid assessment question set further comprises generating a blended co-morbid assessment question set comprising a set of barriers and common care assessment questions comprising assessment questions used to assess a member regardless of the determined medical conditions and that are addressed prior to addressing any assessment questions targeted to a medical condition.

4. The method of claim 1, further comprising:
    determining one or more member responses to one or more assessment questions of the blended co-morbid assessment question set; and
    generating a member activity plan for coaching the member based at least in part on the determined one or more member responses.

5. The method of claim 4, wherein generating the member activity plan comprises generating the member activity plan in real time to enable coaching of the member before completion of every assessment question in the blended co-morbid assessment question set.

6. The method of claim 4, wherein generating the member activity plan comprises:
    determining one or more problems impacting the member's health based at least in part upon the determined one or more member responses; and
    generating a member activity plan comprising content for coaching the member to address the one or more determined problems.

7. The method of claim 6, further comprising determining a priority of each of the determined one or more problems; and
    wherein generating the member activity plan comprises generating a member activity plan comprising content ordered based at least in part upon the determined priorities.

8. An apparatus for facilitating co-morbid care management, the apparatus comprising a processor configured to cause the apparatus to at least:
    determine a plurality of medical conditions affecting a member enrolled in a care management plan;
    activate, based at least in part upon the determined medical conditions, a plurality of member assessment modules, wherein each activated member assessment module is associated with a respective determined medical condition, and wherein each activated member assessment module comprises a set of assessment questions targeted to the medical condition with which the member assessment module is associated;
    generate a blended co-morbid assessment question set based at least in part on the assessment question sets of the activated member assessment modules by blending the assessment question sets of the activated member assessment modules into a blended co-morbid assessment question set; and
    blend the assessment question sets of the activated member assessment modules into a blended co-morbid assessment question set by causing the apparatus to at least:
        determine that the assessment question sets of the activated member assessment modules comprise at least one conflicting assessment question by identifying at least one question that is medically appropriate for a first one of the activated member assessment modules and medically inappropriate for a second one of the activated member assessment modules; and
        when the assessment question sets of the activated member assessment modules comprise at least one conflicting assessment question:
            determine a medically appropriate assessment question based on the at least one conflicting assessment question, wherein the medically appropriate assessment is appropriate for the activated member assessment modules; and
            include the medically appropriate assessment question in the blended co-morbid assessment question set.

9. The apparatus of claim 8, wherein the processor is further configured to cause the apparatus to generate the blended co-morbid assessment question set at least in part by generating a blended co-morbid assessment question set comprising a set of barriers and common care assessment questions comprising assessment questions used to assess a member regardless of the determined medical conditions and that are addressed prior to addressing any assessment questions targeted to a medical condition.

10. The apparatus of claim 8, wherein the processor is further configured to cause the apparatus to:
 determine one or more member responses to one or more assessment questions of the blended co-morbid assessment question set; and
 generate a member activity plan for coaching the member based at least in part on the determined one or more member responses.

11. The apparatus of claim 10, wherein the processor is configured to cause the apparatus to generate the member activity plan by generating the member activity plan in real time to enable coaching of the member before completion of every assessment question in the blended co-morbid assessment question set.

12. The apparatus of claim 10, wherein the processor is configured to cause the apparatus to generate the member activity plan at least in part by:
 determining one or more problems impacting the member's health based at least in part upon the determined one or more member responses;
 determining a priority of each of the determined one or more problems; and
 generating a member activity plan comprising content for coaching the member to address the one or more determined problems, the content being ordered based at least in part upon the determined priorities.

13. The apparatus of claim 8 further comprising at least one memory storing instructions that when executed by the processor cause the apparatus to at least:
 determine a plurality of medical conditions affecting a member enrolled in a care management plan;
 activate, based at least in part upon the determined medical conditions, a plurality of member assessment modules, wherein each activated member assessment module is associated with a respective determined medical condition, and wherein each activated member assessment module comprises a set of assessment questions targeted to the medical condition with which the member assessment module is associated; and
 generate a blended co-morbid assessment question set based at least in part on the assessment question sets of the activated member assessment modules by blending the assessment question sets of the activated member assessment modules into a blended co-morbid assessment question set.

14. A computer program product comprising at least one tangible, non-transitory computer-readable storage medium having computer-readable program instructions stored therein, the computer-readable program instructions comprising:
 program instructions configured to determine a plurality of medical conditions affecting a member enrolled in a care management plan;
 program instructions configured to activate, based at least in part upon the determined medical conditions, a plurality of member assessment modules, wherein each activated member assessment module is associated with a respective determined medical condition, and wherein each activated member assessment module comprises a set of assessment questions targeted to the medical condition with which the member assessment module is associated;
 program instructions configured to generate a blended co-morbid assessment question set based at least in part on the assessment question sets of the activated member assessment modules by blending the assessment question sets of the activated member assessment modules into a blended co-morbid assessment question set; and
 program instructions configured to blend the assessment question sets of the activated member assessment modules into a blended co-morbid assessment question set by:
  determining that the assessment question sets of the activated member assessment modules comprise at least one conflicting assessment question by identifying at least one question that is medically appropriate for a first one of the activated member assessment modules and medically inappropriate for a second one of the activated member assessment modules; and
  when the assessment question sets of the activated member assessment modules comprise at least one conflicting assessment question:
   determining a medically appropriate assessment question based on the at least one conflicting assessment question, wherein the medically appropriate assessment is appropriate for the activated member assessment modules; and
   including the medically appropriate assessment question in the blended co-morbid assessment question set.

15. The computer program product of claim 14, wherein the program instructions configured to generate the blended co-morbid assessment question set further comprise program instructions configured to generate a blended co-morbid assessment question set comprising a set of barriers and common care assessment questions comprising assessment questions used to assess a member regardless of the determined medical conditions and that are addressed prior to addressing any assessment questions targeted to a medical condition.

16. The computer program product of claim 14, further comprising:
 program instructions configured to determine one or more member responses to one or more assessment questions of the blended co-morbid assessment question set; and
 program instructions configured to generate a member activity plan for coaching the member based at least in part on the determined one or more member responses.

17. The computer program product of claim 16, wherein the program instructions configured to generate the member activity plan comprise program instructions configured to generate the member activity plan in real time to enable coaching of the member before completion of every assessment question in the blended co-morbid assessment question set.

* * * * *